(12) United States Patent
Karguth et al.

(10) Patent No.: US 10,603,126 B2
(45) Date of Patent: Mar. 31, 2020

(54) DEVICE FOR ROBOT-ASSISTED SURGERY

(71) Applicant: avateramedical GmbH, Jena (DE)

(72) Inventors: Andreas Karguth, Tuettleben (DE);
Christian Trommer, Schmerfeld (DE);
Marcel Seeber, Jena (DE)

(73) Assignee: avateramedical GmbH, Jena (DE)

(*) Notice: Subject to any disclaimer, the term of this patent is extended or adjusted under 35 U.S.C. 154(b) by 943 days.

(21) Appl. No.: 14/951,965

(22) Filed: Nov. 25, 2015

(65) Prior Publication Data
US 2016/0151115 A1 Jun. 2, 2016

(30) Foreign Application Priority Data
Nov. 27, 2014 (DE) .................. 10 2014 117 408

(51) Int. Cl.
*A61B 34/30* (2016.01)
*A61B 34/37* (2016.01)
(Continued)

(52) U.S. Cl.
CPC .......... *A61B 34/37* (2016.02); *A61B 1/00149* (2013.01); *A61B 18/1492* (2013.01);
(Continued)

(58) Field of Classification Search
CPC ......... A61B 34/30; A61B 34/35; A61B 34/37; A61B 1/00149
See application file for complete search history.

(56) References Cited

U.S. PATENT DOCUMENTS 6,949,106 B2 * 9/2005 Brock ............... A61B 17/0469
606/130
7,331,967 B2 * 2/2008 Lee ........................ A61B 34/71
600/407
(Continued)

FOREIGN PATENT DOCUMENTS

CN 201727584 U 2/2011
CN 203802572 U 9/2014
(Continued)

OTHER PUBLICATIONS

Office Action with Search Report (in Chinese) dated Jul. 24, 2017 regarding Chinese Application No. 201510847822.8 (6 pages).

*Primary Examiner* — Sarah A Simpson
(74) *Attorney, Agent, or Firm* — Harness, Dickey & Pierce, P.L.C.

(57) ABSTRACT

A device for robot-assisted surgery, comprising at least one non-sterile manipulator arm (12) having a coupling unit (100) with drive elements. The device further has an instrument unit (300) which comprises a surgical instrument (500) and a sterile sterile unit (400) for coupling the surgical instrument (500) to the drive elements of the coupling unit (100). The coupling unit (100) comprises a translatory drive element (110, 112) for generating a translatory drive movement and a rotatory drive element (114, 116) for generating a rotatory drive movement. The sterile unit (400) has a translationally driven element (408, 410) couplable to the translatory drive element (110, 112) and a rotationally driven element (412, 414) couplable to the rotatory drive element (114, 116). The device has a sterile lock (200) which is capable of being coupled to the coupling unit (100) and to the sterile unit (400).

16 Claims, 21 Drawing Sheets

(51) Int. Cl.
- *A61B 46/10* (2016.01)
- *A61B 34/35* (2016.01)
- *A61B 90/40* (2016.01)
- *A61B 1/00* (2006.01)
- *A61B 18/14* (2006.01)
- *A61B 17/00* (2006.01)

(52) U.S. Cl.
CPC .............. *A61B 34/30* (2016.02); *A61B 34/35* (2016.02); *A61B 46/10* (2016.02); *A61B 90/40* (2016.02); *A61B 2017/00477* (2013.01); *A61B 2034/301* (2016.02); *A61B 2034/302* (2016.02)

(56) References Cited

U.S. PATENT DOCUMENTS

| | | |
|---|---|---|
| 7,666,191 B2 | 2/2010 | Orban, III et al. |
| 8,074,657 B2 | 12/2011 | Scott et al. |
| 2004/0049205 A1 | 3/2004 | Lee et al. |
| 2006/0067855 A1 | 3/2006 | Mathis et al. |
| 2006/0161138 A1 | 7/2006 | Orban |
| 2006/0235436 A1 | 10/2006 | Anderson et al. |
| 2012/0143211 A1* | 6/2012 | Kishi .............. A61B 34/30 606/130 |

FOREIGN PATENT DOCUMENTS

| | | |
|---|---|---|
| DE | 102006059165 A1 | 8/2007 |
| DE | 102012008535 A1 | 10/2013 |
| DE | 102012008537 A1 | 10/2013 |
| JP | 2007-167644 A | 7/2007 |
| JP | 2009-520573 A | 5/2009 |
| WO | WO-03071971 A2 | 9/2003 |
| WO | WO-2013-067421 A2 | 5/2013 |
| WO | WO-2013-159932 A1 | 10/2013 |
| WO | WO-2014-005689 A2 | 1/2014 |
| WO | WO-2014-162217 A1 | 10/2014 |

* cited by examiner

Section O - O

Section O - O

Section O - O

DEVICE FOR ROBOT-ASSISTED SURGERY

BACKGROUND OF THE INVENTION

Technical Field

The invention relates to a device for robot-assisted surgery, comprising at least one manipulator arm arranged in a non-sterile area and having a coupling unit which has at least a first transmitting means. The device has at least one sterile unit arranged in a sterile area and having at least a second transmitting means and a sterile cover for shielding the manipulator arm from the sterile area.

Discussion

In minimally-invasive surgery, so-called telemanipulator systems, also referred to as robot-assistance systems, are increasingly used. The sterile surgical field is protected against the non-sterile elements of the telemanipulator system by means of a sterile cover. By means of the sterile cover both a contamination of the sterile surgical field and a contamination of the telemanipulator system by body fluids and/or tissue of the operated patient or of the surgical staff is prevented. This reduces the risk of cross-contamination.

SUMMARY OF THE INVENTION

By means of the telemanipulator system surgical instruments and/or endoscopes are controlled in their position and orientation on the basis of user inputs and, in doing so, inevitably come into physical contact with the patient to be operated so that the surgical instruments and/or endoscopes are contaminated with body fluids and/or tissue of the operated patient. At the same time, the surgical instruments have to be coupled mechanically, electrically and/or optically to the telemanipulator system in order to be able to implement an active positioning and orientation of the surgical instrument as well as a desired actuation of a surgical instrument. For this, the surgical instruments, endoscopes or medical devices to be operated have a coupling interface which may be designed as a coupling unit and is also referred to as sterile unit.

The material used during a surgical operation including the employed surgical apparatuses and instruments and the further components of the telemanipulator system can be divided into three categories:

Category 1: The material is sterile and is contaminated during the surgical operation. The material is disposed of after the operation. Thus, there is a one-time use of the material.

Category 2: The material is sterile, is contaminated during the surgical operation and is cleaned and sterilized after the operation. Thus, there is a multiple use of the material. Such materials used multiple times must be designed and produced in accordance with the requirements on a process-capable sterilizability.

Category 3: The material is not sterile. During the surgical operation a contamination of the sterile surgical field is prevented by a sterile cover and over-packaging. At the same time, the non-sterile material is protected against contact with body fluids and/or tissue.

If it is necessary to couple devices of category 1 or category 2 to devices of category 3, then a sterile interface is required which prevents contamination of the devices of category 1 or category 2 by the non-sterile devices of category 3 and, vice versa, prevents a contamination of the devices of category 3 since these are generally technically designed as autoclavable components that cannot be sterilized. The realization of devices as autoclavable components that can be sterilized requires a particular technical design of the device for the sterilization process so that a higher development effort as well as considerable validation effort for proving the effectiveness of the sterilization process are necessary for this. For such a proof, it is in particular necessary, multiple times in succession, to contaminate and sterilize the device and to perform an effectiveness check of the sterilization as well as a functionality check after sterilization. Here, proof has to be furnished that after each sterilization the devices are reliably sterilized and thus could be used again.

From document U.S. Pat. No. 7,666,191 B1, a telemanipulator system is known in which the non-sterile manipulator arms are covered by means of a sterile drape. The coupling unit of the manipulator arm comprises four rotation actuators which are coupled to a first side of a sterile adaptor integrated in the sterile drape. By means of the sterile adaptor, the rotary motions of the four rotation actuators of the coupling unit of the manipulator arm are engaged with four rotatably mounted transmitting means integrated in the sterile adaptor. On the sterile outside surface of the sterile adaptor these sterile transmitting means on the outside surface of the sterile adaptor can be engaged with driven elements of the sterile surgical instrument. Further, via this sterile adaptor electrical signals can be transmitted between the inside and the outside of the sterile adaptor.

Thus, by means of the sterile adaptor it is prevented that the rotation actuators and the electrical connections of the sterile surgical instrument come into direct contact with the rotation actuators and the electrical connections of the coupling unit of the non-sterile manipulator arm. A contamination of the surgical instrument by the contact with non-sterile parts of the manipulator arm is prevented by the sterile adaptor. In this solution it is, however, essential that the sterile adaptor must have rotatably mounted transmitting means as well as transmitting means for transmitting electrical signals, as a result whereof the adaptor is costly in production and is susceptible to interference. In particular, it is costly to guarantee the rotatability of the transmitting means when the transmitting means come into contact with body fluid.

Basically, each element in the chain of functions for coupling the manipulator arm and the instrument is a possible source of errors and involves additional costs. The sterile adapter itself is provided as part of the sterile drape for a one-time use.

From document U.S. Pat. No. 8,074,657 B2, a further sterile adapter is known which comprises an actuator unit for transmitting mechanical energy to a surgical instrument coupled to the sterile adapter.

It is the object of the present invention to specify a device and an arrangement for robot-assisted surgery, in which a sterile coupling of a manipulator arm arranged in a non-sterile area to a sterile unit arranged in a sterile area is easily possible, wherein by the coupling a reliable mechanical force and torque transmission and/or optical transmission and/or electrical signal and/or energy transmission is possible between the manipulator arm and the instrument unit which in particular comprises a sterile unit and a surgical instrument connected thereto.

This object is solved by a device for robot-assisted surgery having the features of claim 1 and by an arrangement having the features of claim 15. Advantageous developments of the invention are specified in the dependent claims.

By providing a translatory drive element for generating a translatory drive movement and a rotatory drive element for generating a rotatory drive movement in the coupling unit and by providing a translationally driven element couplable to the translatory drive element and rotationally driven element couplable to the rotatory drive element an easy drive of the instrument unit which in particular comprises a sterile unit and a surgical instrument connected thereto is possible. By means of the sterile lock provided in the sterile cover, in turn, a safe sterile shielding of the drive elements independent of the coupling unit is preferably possible when the sterile unit is not connected to the sterile lock. The sterile lock also shields the drive elements after the sterile unit has been separated from the sterile lock. As a result, a safe sterile covering of the non-sterile elements of the manipulator arm against the sterile area is easily possible.

By means of the rotatory drive unit and the translatory drive unit, for example the rotation of an instrument and the bending of the instrument tip or the rotation of the instrument and a grasping movement can easily be performed. Alternatively, the instrument shaft can be rotated and a grasping movement of the instrument can be performed.

It is particularly advantageous when by means of the translatory drive element coupled to the translationally driven element the translatory drive movement can be transmitted to the translationally driven element. By means of the rotatory drive element coupled to the rotationally driven element the rotatory drive movement can be transmitted to the rotationally driven element.

A rotatory drive element is generally a drive element that can perform a rotatory drive movement or a rotary motion and is driven directly or indirectly in particular by a drive motor for this purpose.

A rotationally driven element is generally a driven element couplable to the rotatory drive element and performing a rotatory movement or a rotary motion when the rotatory drive element coupled to the driven rotatory element performs a rotatory drive movement or rotary motion.

A translatory drive element is generally a drive element that can perform a translatory drive movement or a translational motion and is directly or indirectly driven in particular by a drive motor for this purpose.

A translationally driven element is generally a driven element that is couplable to a translatory drive element and that performs a translatory movement or translational motion when the translatory drive element coupled to the driven translatory element performs a translatory drive movement or translational motion. When coupling a drive element to a driven element there is preferably a direct contact of one drive element with a complementary driven element for transmitting the drive movement. This can in particular be realized by a positive and/or non-positive connection and/or a magnetic coupling between the respective driven element and the drive element.

It is advantageous when the sterile lock connected to the coupling unit and to the sterile unit provides access to the drive elements such that the translatory drive element is couplable to the translationally driven element and the rotatory drive element is couplable to the rotationally driven element. A coupling between a drive element and a driven element is in particular realized by a direct engagement, such as a positive connection, or a non-positive connection.

Further, it is advantageous when the sterile unit comprises a sterile cover which shields the driven elements in a sterile manner before the sterile unit is connected to the sterile lock and preferably after the sterile unit has been separated from the sterile lock. The sterile lock provides access to the driven elements when the sterile lock is connected to the coupling unit and to the sterile unit. As a result, an easy handling of the surgical element and of the manipulator arm is possible since the sterile unit with the surgical instrument is easily connectable and again disconnectable to and from the coupling unit of the manipulator arm, respectively, wherein it is guaranteed that the driven elements are shielded in a sterile manner when the sterile unit is not connected to the sterile lock and is not coupled to the coupling unit, respectively. As a result, a safe handling of the instrument unit in the sterile area is possible so that the instrument unit can be placed in the sterile area even after contact of the driven elements with the non-sterile drive elements, without the sterile area being contaminated thereby.

Further, it is advantageous when the sterile lock comprises a sterile cover that shields the drive elements in a sterile manner before the sterile unit is connected to the sterile lock and preferably after the sterile unit has been separated from the sterile lock. The sterile lock provides access to the drive elements when the sterile lock is connected to the coupling unit and to the sterile unit. Thus, it is guaranteed that the usually non-sterile drive elements of the coupling unit are shielded from the sterile area by means of the sterile lock whenever the sterile unit of the instrument unit is not connected to the sterile lock, in particular after the sterile unit of the instrument unit has again been separated from the sterile lock. The sterile lock provides access to the drive elements when the sterile lock is connected to the coupling unit and to the sterile unit. As a result, a safe shielding of the non-sterile coupling unit, in particular of the non-sterile drive elements, from the sterile area is achieved. When coupling the sterile unit to the sterile lock, preferably an access opening of the sterile lock covered in a sterile manner is uncovered so that the drive elements can be brought into direct contact with the driven elements, in particular in direct engagement with one another.

The sterile cover of the sterile lock for covering the drive elements in a sterile manner and/or the sterile cover of the sterile unit for shielding the driven elements in a sterile manner can be a jalousie, a roller blind, a rotatable disk provided with an opening and/or a flap. As a result, an easy safe closing and opening of at least one access opening to the drive elements or the driven elements is easily possible.

It is particularly advantageous when the translatory drive element is a first translatory drive element and the rotatory drive element is a first rotatory drive element and when the translationally driven element is a first translationally driven element and when the rotationally driven element is a first rotationally driven element. The coupling unit comprises a second translatory drive element for generating a translatory drive movement and a second rotatory drive element for generating a rotatory drive movement. The sterile unit has a second translationally driven element couplable to the second translatory drive element and a second rotationally driven element couplable to the second rotatory drive element. The sterile lock connected to the coupling unit shields the first and the second translatory drive element and the first and the second rotatory drive element in a sterile manner before the sterile unit is connected to the sterile lock and preferably after the sterile unit has been separated from the sterile lock.

Generally, the drive movements of all drive elements are independent of each other, in particular are not mechanically coupled. All drive movements of the drive elements are controlled by means of a control unit and preferably electronically monitored.

Further, it is advantageous when the first and/or second translationally driven element is movable into an initial position by means of the restoring force of an elastically deformable element and when this restoring force moves the respective translationally driven element into its initial position after the separation of the sterile unit from the sterile lock. As a result, a defined position of the translationally driven elements is easily possible when the sterile unit is connected or re-connected to the sterile lock and when the drive elements are thus coupled to the driven elements. Here, the restoring force is at least so high that it restores the displacement of the surgical instrument caused by the translatory drive elements into an initial position when no further forces acting on the instrument impede or prevent the restoring.

Further, it is advantageous when the coupling unit has at least one position sensor for detecting at least one rotation angle position of a first and/or second rotationally driven element. Preferably, the device comprises a first position sensor for detecting at least one rotation angle position of the first rotationally driven element and a second position sensor for detecting at least one rotation angle position of the second rotationally driven element. In the case of an initialization, then the first rotationally driven element is rotated by means of the first rotary drive element until the first position sensor detects a defined angular position of the rotationally driven element. In particular, the rotationally driven element comprises at an angular position a projection or a recess detectable by means of the first position sensor, which can be detected by means of the position sensor when the projection or the recess are arranged opposite to the position sensor. As a result, the angular position of the rotationally driven element can be detected and, based thereon, the further drive of the rotationally driven element can be monitored by means of a control unit such that the angular position of the rotationally driven element is known at any time and is taken into account in the further control.

In the same manner, a defined rotation angle position of the second rotationally driven element can be detected by means of the second position sensor so that by means of a control unit the drive of the second rotationally driven element is monitored such that its rotation angle position is known at any time and can be taken into account in the further control.

Further, it is advantageous when the coupling unit moves the translatory drive element into an initial position after the sterile unit has been separated from the sterile lock. As a result, the translatory drive element arranged in its initial position can automatically directly be engaged with the translationally driven element arranged in its initial position when connecting the sterile unit to the sterile lock that is connected to the coupling unit.

A translatory drive element can, for example, be formed by a fork, the tines of which engage with a circumferential groove of the translationally driven element. This groove is preferably a circumferential groove so that the translationally driven element can be rotated in the fork together with elements of the instrument unit for rotatory force transmission, such as an instrument shaft.

It is particularly advantageous when the coupling unit moves the first translatory drive element into its initial position after the sterile unit has been separated from the sterile lock. The first translatory drive element arranged in its initial position is automatically directly engageable with the first translationally driven element arranged in its initial position when connecting the sterile unit to the sterile lock that is connected to the coupling unit.

Further, it is advantageous when the coupling unit moves the second translatory drive element into its initial position after the sterile unit has been separated from the sterile lock. The second translatory drive element arranged in its initial position is automatically directly engageable with the second translationally driven element arranged in its initial position when connecting the sterile unit to the sterile lock that is connected to the coupling unit.

Thus, it is particularly advantageous when the first and/or second translationally driven element is moved into its initial position by means of the elastically deformable element after the separation of the sterile unit from the sterile lock and when the first and/or second translatory drive element is moved into its initial position by means of the drive elements after the separation of the sterile unit from the sterile lock. In this way, it is guaranteed that a re-connection of the sterile unit to the sterile lock and the coupling of the drive elements to the driven elements caused thereby is possible without difficulties.

Further, it is advantageous when the driven elements are arranged successively along the longitudinal axis of the surgical instrument and when the driven elements are arranged from the proximal end of the surgical instrument preferably in the order first rotationally driven element, first translationally driven element, second rotationally driven element, second translationally driven element. Optionally, in this order, electrical contacts and/or an optical interface can subsequently be arranged along the longitudinal axis. In the connected state of the sterile unit and the sterile lock as well as the sterile lock and the coupling unit, drive elements complementary to the driven elements, electrical contacts complementary to the electrical contacts and an optical interface complementary to the optical interface are arranged on the opposite side. As a result, a compact and cost-efficient structure both of the sterile unit and of the coupling unit is possible.

Further, it is advantageous when the first rotationally driven element is connected in a rotationally-fixed manner to the outer instrument shaft for rotation thereof. As a result, a rotation of the outer instrument shaft about its longitudinal axis by the first rotary drive element via the first rotationally driven element is easily possible.

Further, the first translationally driven element can be connected to a first inner instrument shaft arranged in the outer instrument shaft so as to be movable lengthwise in the direction of the longitudinal axis of the outer instrument shaft, wherein when the first inner instrument shaft is moved, the instrument tip is pivotable about an axis of rotation which is preferably orthogonal to the longitudinal axis of the surgical instrument. As a result, in particular an instrument tip arranged at the proximal end of the surgical instrument can be bent when the translationally driven element is driven by means of the first translatory drive unit.

Further, the second rotationally driven element can be connected in a rotationally-fixed manner to a second inner instrument shaft arranged in the first inner instrument shaft, wherein by the rotation of the second inner instrument shaft a rotation of the end effector independent of the outer instrument shaft is caused. Instead of the second inner instrument shaft or within the second inner instrument shaft, a rotary and push rod can be provided which in particular may be elastically deformable and, for example, designed as a wire cable.

The second translationally driven element can be connected to the second inner instrument shaft arranged movably lengthwise relative to the first inner instrument shaft for actuation of the end effector. As a result, in particular an actuation of the end effector of the instrument tip can be accomplished easily.

The axis of rotation about which the end effector is pivotable is preferably orthogonal to the longitudinal axis of the inner and the outer instrument shafts. Preferably, the inner and the outer instrument shafts are rotationally fixed to one another. Further, the outer instrument shaft and the inner instrument shafts have the same longitudinal axis, i.e. they are coaxial.

Further, it is advantageous when the sterile unit has at least one first slip ring which is coaxial to the second inner instrument shaft and is connected thereto in an electrically conductive manner. In this way, electrical energy can be passed from the coupling unit via the slip ring to the end effector to supply, for example, a monopolar surgical instrument for high-frequency surgery with electrical energy.

It is particularly advantageous when the sterile unit has a second slip ring that is coaxial to the first inner instrument shaft and is electrically connected thereto, wherein the second inner instrument shaft and the first inner instrument shaft are arranged in an electrically insulated manner. Preferably, also the first inner instrument shaft and the outer instrument shaft are arranged to one another in an electrically insulated manner. As a result, a transmission of electrical energy for a bipolar surgical instrument can safely be provided with electrical energy.

It is particularly advantageous when the surgical instrument has an end effector with two arms movable relative to each other by means of the second inner instrument shaft and when the arms are arranged to each other in an electrically insulated manner. The arms are each connected in an electrically conductive manner to an electric cable, which cables are guided in the second inner instrument shaft or in a third instrument shaft arranged in the second inner instrument shaft. The cable is preferably an insulated wire for transmitting electrical energy between the sterile unit and the end effector. As a result, an easy and safe transmission of high-frequency electrical energy from the sterile unit to the instrument tip or to the end effector is easily possible. Further, a first arm of the end effector can be moved actively for producing the relative movement of the arms to each other and a second arm of the end effector can be fixed. The arms are preferably gripping arms, clamping arms and can each comprise a cutting blade and/or a clamping area.

Further, it is advantageous when the sterile unit has a first bearing for rotatably mounting the outer instrument shaft relative to a housing of the sterile unit couplable to the sterile lock and when the sterile unit has at least a second bearing for rotatably mounting the rotary and push rod with respect to the housing of the sterile unit. As a result, an easy and safe mounting of the elements of the instrument shaft and of the driven elements is easily possible.

Further, it is advantageous when the coupling unit is connected via power supply lines to a control circuit of a control unit and/or a power supply unit, preferably via at least one plug connector, for supplying at least one electric drive unit arranged in the coupling unit. Preferably, four electric drive units are arranged in the coupling unit, which each drive a drive element such as the first rotatory drive element, the second rotatory drive element, the first translatory drive element and/or the second translatory drive element.

Further, the control unit can be coupled to the coupling unit via at least one control and/or signal unit, preferably via a plug connector for coupling the control unit. Further, the coupling unit can be connected to at least one power supply line for supplying high-frequency electrical energy for the high-frequency surgery. The high-frequency electrical energy is preferably transmitted via slip ring contacts of the coupling unit to the slip rings of the sterile unit. In this way, an easy use of surgical instruments for high-frequency surgery is possible, wherein the power supply of the surgical instrument for high-frequency surgery is accomplished without separate connections simply by coupling the sterile unit to the coupling unit.

Further, the sterile unit and the coupling unit can have transmitting means for the optical and/or electrical transmission of measuring and/or control signals and/or image information, for providing an optical channel for illumination and/or for image transmission between the sterile unit and the coupling unit.

In the invention, in particular in the case of a connection of the sterile unit to the sterile lock the drive elements previously covered in a sterile manner are uncovered for a coupling with the driven elements. When separating the sterile unit from the sterile lock, at least the first transmitting means is again shielded in a sterile manner. Preferably, the sterile lock is already connected to the coupling unit when connecting and separating the sterile unit with or from the sterile lock, respectively. Preferably, the sterile lock remains coupled to the coupling unit throughout the entire period of time of the surgical operation, wherein the instrument unit with the sterile unit can be separated from and re-connected to the coupling unit of the manipulator arm multiple times or can be replaced by another instrument unit with a further sterile unit.

By means of the invention it is in particular possible to provide the sterile lock without mechanical and/or electrical transmitting means so that both a safe sterile shielding of the non-sterile manipulator arm and the non-sterile coupling unit as well as a safe coupling of the drive units to the driven units without any interconnection of further transmitting means, in particular without interconnecting further mechanical transmitting means is possible. The sterile cover in particular comprises a sterile flexible material, such as a sterile foil, and the at least one sterile lock.

It is advantageous when the sterile unit has at least one sterile flap which in a closed state shields the second transmitting means in a sterile manner. When connecting the sterile unit to the sterile lock then each time a movement of the lock flap and the sterile flap from the closed state into the open state takes place so that a direct transmission between the first transmitting means and the second transmitting means through an opening uncovered by the lock flap and the sterile flap in the open state is possible. When separating the sterile unit from the sterile lock, a movement of the lock flap and the sterile flap each time from the open state into the closed state takes place so that the lock flap shields the first transmitting means after separation and the sterile flap shields the second transmitting means from the sterile area after separation.

According to the definition in the introductory part of the description, the sterile unit is material of category 1 and 2 and is thus sterile.

Further, it is advantageous when the coupling unit is connectable to a first connecting area of the sterile lock and when the sterile unit is connectable to a second connecting area of the sterile lock. The first connecting area and the second connecting area are preferably arranged on sides of the sterile lock facing away from each other. As a result, an easy coupling and thus an easy handling both of the sterile cover and of the sterile unit before, during and after the surgical operation is possible. Further, it is particularly advantageous when the second connecting area is designed as a receiving area in which the sterile unit is receivable at least in part upon connection with the second connecting area. As a result, an easy and safe connection between the sterile unit and the sterile lock can be established. In particular, the sterile unit can at least in part be pressed into the receiving area and be locked therein.

Further, it is advantageous when the sterile lock has a third connecting area with which the flexible cover is connectable, wherein the third connecting area is arranged preferably circumferentially around the sterile lock, in particular on the circumferential surface, preferably between the first and second connecting area. By means of the sterile lock an easy connection of the sterile area and the non-sterile area for coupling the coupling unit to the sterile unit is established without the sterile unit being contaminated such that it can no longer remain in the sterile area after a separation from the sterile lock.

Preferably, the coupling unit is arranged at the proximal end of the manipulator arm.

Further, it is advantageous when the first connecting area of the sterile lock is connectable to the coupling unit via a first releasable snap-in connection and the second connecting area of the sterile lock is connectable to the sterile unit via a second releasable snap-in connection. As a result, the sterile lock is safely connectable to both the coupling unit and the sterile unit and is easily separable from these so that an easy handling both of the sterile cover with the sterile lock and of the sterile unit, in particular during a surgical operation, is possible.

It is particularly advantageous when the coupling unit comprises at least one coupling sensor which detects the presence of a sterile unit that is correctly connected to the sterile lock. Further, the device has a sterile unit which only allows a transmission between the first transmitting means and the second transmitting means when a sterile unit that is correctly connected to the sterile lock has been detected by means of the coupling sensor. In a further advantageous embodiment the coupling sensor detects by means of a detection element which is provided on the sterile unit and which, when connected to the sterile lock, projects up into the first connecting area with which the coupling unit is connected that both the sterile unit is correctly connected to the second connecting area and the coupling unit is correctly connected to the first connecting area. The control unit preferably only releases or only permits a drive of the driven elements by the drive elements when the coupling sensor has detected a correct connection between the sterile unit and the second connecting area and the coupling unit and the first connecting area.

In addition, by means of the coupling sensor it can easily be detected whether at least the sterile unit is correctly connected to the sterile lock so that then it can be assumed that the sterile unit is correctly connected to the sterile lock and, via the sterile lock, is correctly connected to the coupling unit of the manipulator arm. As a result, a safe drive of the driven elements by the drive elements is possible.

The surgical instrument preferably comprises at least one end effector insertable into an orifice of the body of a patient, such as a clamp, a pair of scissors, a grasper, a needle holder, a micro dissector, a clamping device, a staple applier, a rinsing and/or an aspiration device, a cutting blade, a cauterization probe, a catheter and/or a suction nozzle. As a result, the surgical instrument can optionally have different end effectors which can be used for common minimally-invasive surgery, in particular in laparoscopic surgery. However, also other surgical instruments can be used additionally or alternatively. In particular, the surgical instrument can also be an optical surgical instrument such as an endoscope, which then has further optical and electrical transmitting means or interfaces such as electrical contacts for camera control or for image data transmission, optical fiber connections, in particular for illumination.

A second aspect of the invention relates to an arrangement for robot-assisted surgery, in particular to a telerobot-assisted procedure within a sterile field by means of a sterile surgical instrument. This arrangement comprises at least one device according to claim 1 or according to an aforementioned development, a display unit which outputs in real time at least one image of the field of operation in which the end effector of the surgical instrument can be, preferably as an image sequence, and at least one device for the input of at least one input command. The arrangement further has a control unit which positions the manipulator arm and the sterile unit connected via the sterile lock to the coupling unit of the manipulator arm dependent on the input command by means of at least one drive unit. As a result, an easy control of the manipulator arm for positioning the sterile unit and/or an actuation for actuating the sterile unit is easily possible. Preferably, the input device has an actuating element actuatable by a user, such as a surgeon, wherein the input device detects a change of position in space of the actuating element and generates an input command corresponding to the detected change of position in space. Dependent on the input command the control unit generates at least one control command by which the same or a scaled down change of position in space of at least an end of the sterile unit and/or of the surgical instrument, at the distal end of which the sterile unit is arranged, is caused and/or by which an actuation or a reduced actuation of the surgical instrument, at the distal end of which the sterile unit is arranged, is caused. As a result, an easy positioning and/or actuation of the surgical instrument by an operator who is remote from the patient in the operating room or outside the operating room is easily possible. As an output of an image in real time the immediate output of an image detected by means of an image detection unit preferably as a video sequence without delays going beyond the delays occurring during image processing.

Further, it is advantageous when the arrangement has several devices for robot-assisted surgery according to claim 1 or according to a mentioned development. The input device has preferably at least two actuating elements actuatable by a user, wherein the input device detects a change of position in space of each actuating element and generates each time an input command corresponding to the detected change of position in space. Dependent on each input command, the control unit generates at least one control command each by which the same or a scaled up/down change of position in space of at least one end of a surgical instrument, at the distal end of which the sterile unit is arranged, of the device for robot-assisted surgery assigned to the respective actuating element at the point in time of the actuation is caused and/or by which an actuation or a scaled actuation of this surgical instrument is caused. As a result, the operation can be performed with several instruments which are present in the operating field at the same time or which, in the case of laparoscopic surgeries, are present in the abdominal cavity of the patient at the same time.

The sterile lock can have two lock flaps, and the sterile unit can have two sterile flaps.

In all described embodiments, the sterile lock forms no part of the chain of functions for transmitting electrical energy, of electrical or optical signals and/or mechanical energy between the manipulator arm and the sterile unit. Rather the sterile lock can comprise a fixed form part and a lock flap system comprising at least the lock flap, which shields non-sterile drive elements of the coupling unit such that this one and the entire coupling unit are covered in a sterile manner relative to the sterile surrounding after mounting the sterile cover with the sterile lock. The opening mechanism of the lock flap system is preferably designed such construction-wise that it cannot be opened from outside by inadvertent actuation. Further, also the driven elements can be shielded by a sterile housing of the sterile unit and in particular by the at least one sterile flap of the sterile unit in a sterile manner.

The drive elements and the driven elements are preferably designed such that a laparoscopic surgical instrument can be moved in altogether four degrees of freedom, namely:

1. Rotation of the instrument shaft
2. Rotation of the instrument tip independent of the instrument shaft
3. Bending of the instrument tip relative to the instrument shaft
4. Actuation of the surgical instrument, in particular for generating a relative movement of two elements arranged movably to each other, such as the grasping motion of the instrument tip or of blades of scissors.

During the connection to the sterile lock, the sterile housing of the sterile unit is preferably pressed into a receiving area of the second connecting area and secured by means of a mechanical detent on the sterile lock against inadvertent removal. The mechanical detent thus creates a snap-in connection between the sterile lock and the sterile unit. For separating the sterile unit from the sterile lock an unlocking button is actuated manually so that the sterile unit is separated from the second connecting area, preferably can be removed from the receiving area of the second connecting area.

In general, an end of an arbitrary element facing the patient is considered as proximal. In general, an end of an element facing away from the patient is considered as distal.

Further features and advantages result from the following description which explains the invention in more detail on the basis of embodiments in connection with the enclosed Figures.

DRAWINGS

DETAILED DESCRIPTION

Figure 1:
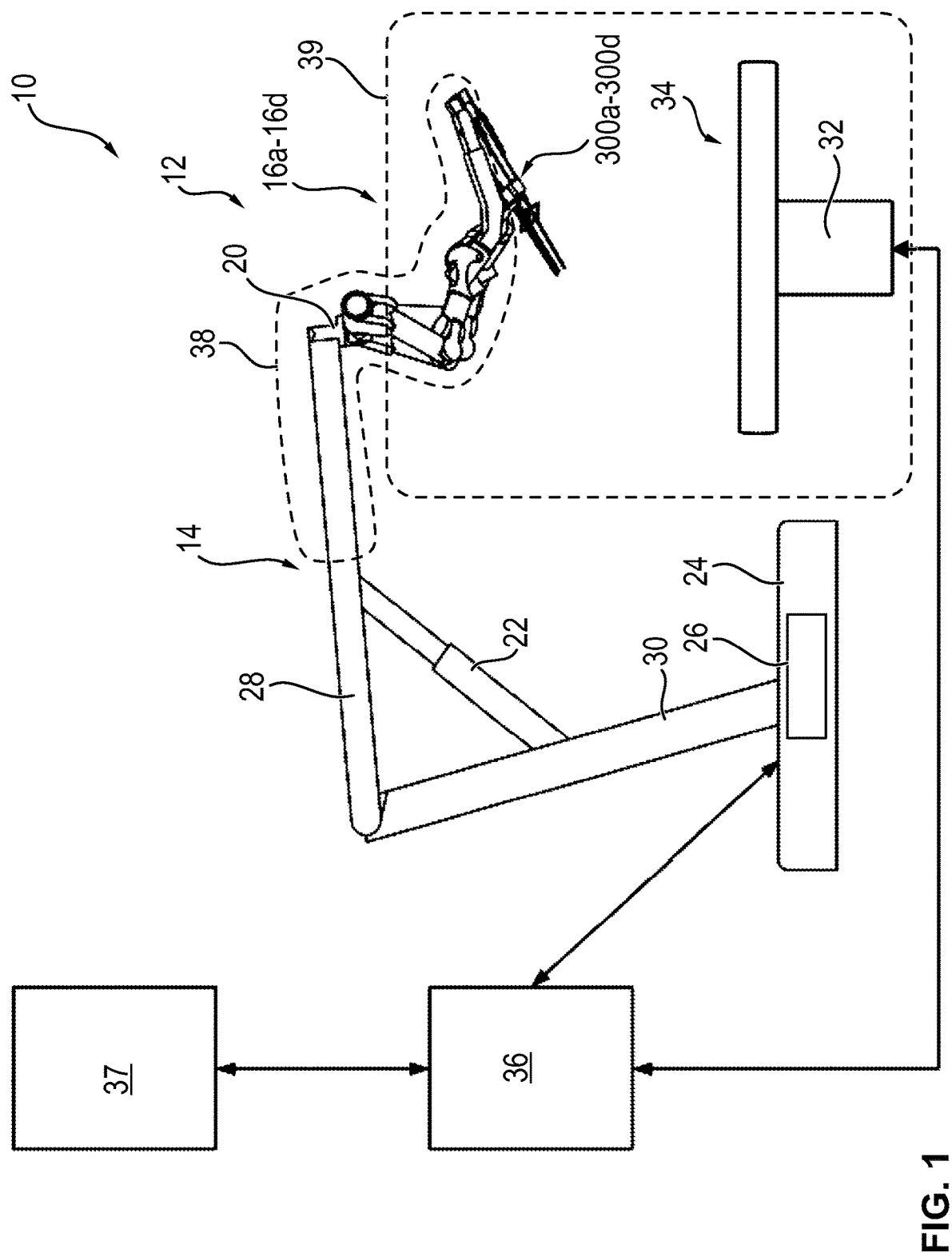
FIG. 1 shows a schematic illustration of a system for robot-assisted surgery comprising a manipulator having four manipulator arms to which one sterile unit each of an instrument unit is connectable.

FIG. 1 shows a schematic illustration of a system 10 for robot-assisted surgery with a manipulator 12 having a mount 14 and four manipulator arms 16a to 16d. In other embodiments, the manipulator 12 can also have more or less manipulator arms 16a to 16d. Each manipulator arm 16a to 16d is connected to a sterile instrument unit 300a to 300d via a coupling unit of the manipulator arm 16a to 16d. The instrument unit 300a to 300d is sterile and comprises in addition to the sterile unit for coupling the instrument unit 300a to 300d to the coupling unit of the manipulator arm 16a to 16d, a surgical instrument, in particular an end effector, wherein the end effector can be moved and/or actuated by means of the coupling unit of the manipulator arm 16a to 16d. Alternatively to the surgical instrument, the instrument unit 300a to 300d can also comprise an optical instrument, in particular an endoscope, and/or a medical device, in particular for the application of a medicine, for dispensing a rinsing fluid and/or for aspiration of rinsing fluid and/or secretion.

The mount 14 has a mount base 24 standing on the floor of an operating room. The manipulator arms 16a to 16d are connected to a mount head 20 of the mount 14. In other embodiments, the mount can also be a ceiling mount.

The position of the mount head 20 is adjustable by means of a first drive unit 22 and by means of a second drive unit 26 arranged in the mount base 24. By means of the drive unit 22, mount arms 28, 30 are movable relative to each other. By means of the drive unit 26, the inclination of the mount arm 30 relative to the support surface of the mount base 24 can be changed and/or the mount arm 30 can be rotated about a vertical axis of rotation. In general, the positioning of the mount head 20 takes place prior to a surgery of a patient. During the surgery, the position of the mount head 20 relative to the column 32 of an operating table 34 normally remains unchanged. The manipulator 12 is controlled by means of a control unit 36. The control unit 36 is connected via a data and/or control line to an input and output unit 37 which in particular outputs an image of the operation field to a user in real time by means of at least one display unit. The user makes user inputs by which the instrument units 300a to 300d are positioned and actuated during the operation of the patient. The input and output unit 37 thus serves as a human machine interface.

The control unit 36 is further connected via a control and/or data connection to a non-illustrated control unit of the operating table 34. Via this control and/or data connection it is guaranteed that the position of the patient support surface or of segments of the patient support surface of the operating table 34 can only be changed when this is safely possible for a patient to be operated owing to the positioning of the instruments units 300a to 300d.

The operating table 34 as well as the instrument units 300a to 300d are arranged in a sterile operating area 39. The manipulator arms 16a to 16d and the mount 14 are not sterile. The areas of the manipulator 12 projecting into the sterile operating area 39, i.e. the manipulator arms 16a to 16d, the mount head 20 and a part of the mount arm 28 are packed in a sterile manner in a sterile flexible cover 38, such as a sterile foil, indicated by means of the broken line, so that they can be safely arranged in the sterile operating area 39. The input and output unit 37 is arranged outside the sterile area 39 and thus does not have to be packed in a sterile manner.

In a large number of surgeries the instrument units 300a to 300d have to be changed several times during the surgery owing to the course of the surgery. Thus, between the manipulator arm 16a to 16d and the instrument unit 300a to 300d a sterile interface has to be provided which guarantees that the non-sterile parts of the coupling unit of the manipulator arm 16a to 16d are covered in a sterile manner even after the separation of the instrument unit 300a to 300d. In addition, elements of the instrument unit 300a to 300d contaminated by a contact of the sterile elements of the coupling unit of the manipulator arm 16a to 16d have to be covered in a sterile manner after the separation of the instrument unit 300a to 300d from the manipulator arm 16a to 16d so that the instrument unit 300a to 300d can be placed in the sterile area 39 without contaminating further elements in the sterile area 39. For this, a sterile lock is provided between the coupling unit of the manipulator arm 16a to 16d and the instrument unit 300a to 300d, which comprises at least one lock flap that is closed when no instrument unit 300a to 300d is connected to the sterile lock so that then the non-sterile coupling unit is shielded from the sterile area 39 by means of the flexible sterile cover 38 and the sterile lock integrated therein.

Figure 2:
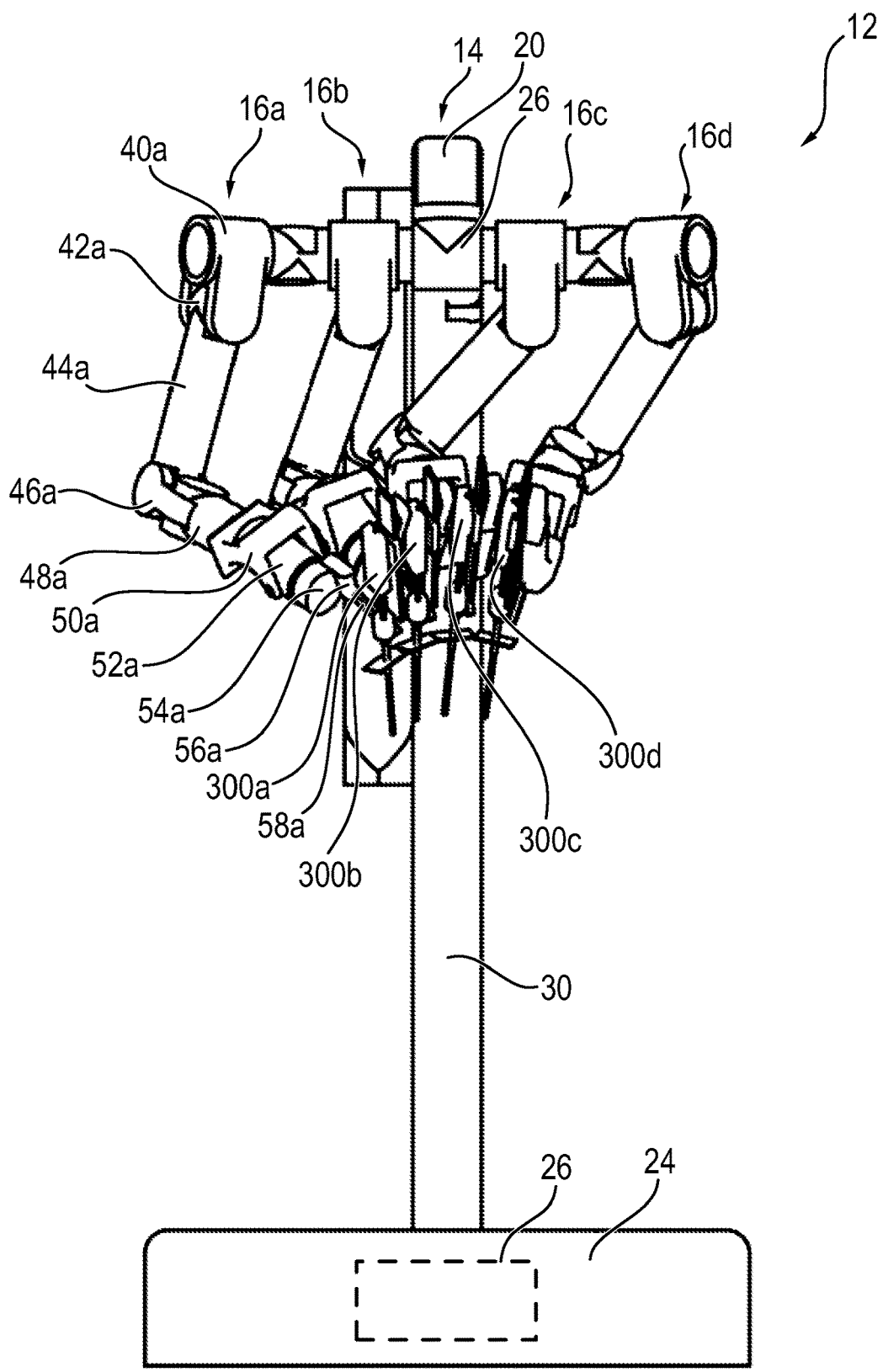
FIG. 2 shows a front view of the manipulator illustrated in FIG. 1.

In FIG. 2, a front view of the manipulator 12 according to FIG. 1 is shown. The manipulator arms 16a to 16d of the manipulator 12 each have several segments 40a to 58a which are movable relative to each other by means of integrated drive units so that the instrument units 300a to 300d can be positioned accurately without collision. The sterile covers 38 for shielding a portion of the manipulator arms 16a to 16d are not illustrated in FIG. 2. The segments of the manipulator arm 16a are identified with the reference signs 40a to 58a. The further manipulator arms 16b to 16d have the same structure and have the segments 40b to 58b, 40c to 58c and 40d to 58d not identified in FIG. 2 for reasons of clarity. The same elements of the manipulator arms 16a to 16d are identified with the same reference sign and the additional letter for distinguishing manipulator arms 16a to 16d. The statements made in the following description refer to the manipulator arm 16a and the instrument unit 300a which are identified in the following with manipulator arm 16 and instrument unit 300. The segments 40a to 58a of the manipulator arm 16a are identified in the following as segments 40 to 58. The explanations, however, apply in the same manner to the identically constructed manipulator arms 16b to 16d and the instrument units 300b to 300d. Elements having the same structure and/or the same function are identified with the same reference signs.

Figure 3:
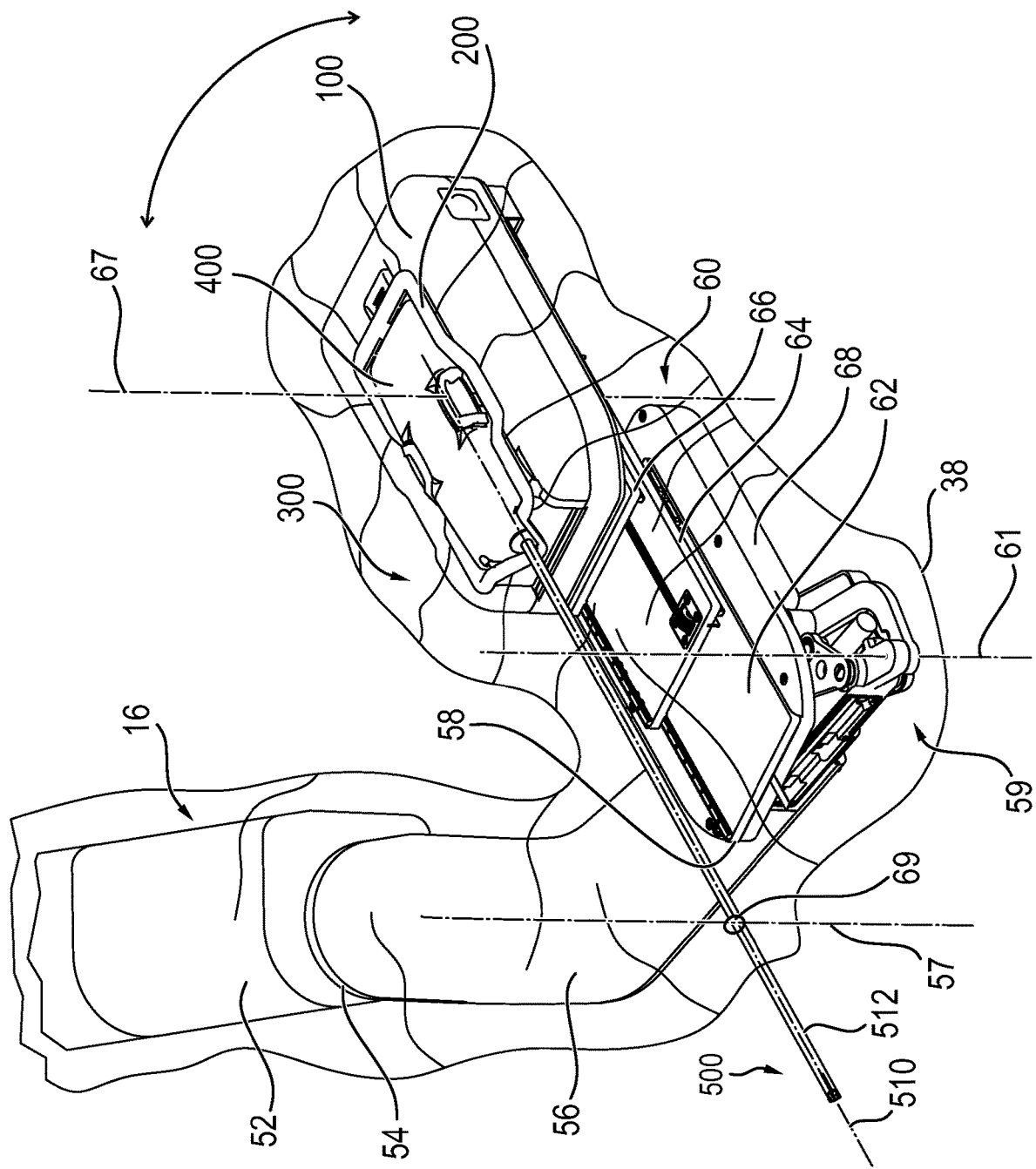
FIG. 3 shows a perspective illustration of a portion of a manipulator arm with a coupling unit for coupling the manipulator arm to an instrument unit comprising a sterile unit, a sterile lock coupled to the coupling unit, and a sterile unit of the instrument unit coupled to the sterile lock.

FIG. 3 shows a perspective illustration of a portion of the manipulator arm 16 with a coupling unit 100 for coupling the manipulator arm 16 to the instrument unit 300 comprising a sterile unit 400. For this, the coupling unit 100 is connected to a sterile lock 200 integrated in the sterile cover 38. The sterile lock 200 is couplable and again separable both to the coupling unit 100 and to the sterile unit 400. In FIG. 3, the sterile lock 200 is illustrated so as to be coupled both to the coupling unit 100 and to the sterile unit 400. The coupling unit 100 is arranged at the distal end of the telescopic arrangement 60.

The telescopic arrangement 60 has sections 62, 64, 66 movable to each other and is illustrated in FIG. 3 in an extended state. The sections 62, 64, 66 of the telescopic arrangement 60 can be retracted and extended by means of a drive unit 68 so that a surgical instrument 500 of the instrument unit 300 can be moved along the longitudinal axis 510 of the instrument shaft 512 together with the coupling unit 100, the sterile lock 200 and the sterile unit 400. By means of a drive unit integrated into the segment 52, the segment 54 can be rotated about the axis of rotation 57 together with the segment 56 designed as an articulated arm. The segment 58 is connected to the segment 56 via a coupling gear mechanism 59 so that the segment 58 can be pivoted about the axis of rotation 61 after activation of a drive unit connected to the coupling gear mechanism 59. Further, the coupling unit 100 is arranged rotatably about the axis of rotation 67 relative to the segment 66 via a coupling gear mechanism not visible in FIG. 3. This coupling gear mechanism, too, is drivable via a drive unit connected to this coupling gear mechanism so that when this drive unit is activated, the coupling unit 100 is rotated about the axis of rotation 67. Here, the drive units of the coupling gear mechanisms are driven such that the longitudinal axis 510 of the instrument shaft 512 is pivoted about a pivot point 69 fixed in space when the manipulator arm 16 and its segments are moved so that the longitudinal axis 510 of the instrument shaft inserted into a patient preferably through a trocar during a surgery is then rotated about the pivot point 69 so that it is guaranteed that by a movement of the instrument 500 only a slight stress on the patient at the entrance point of the instrument 500 into the patient is exerted and in particular an injury of the patient at the point of entering of the instrument shaft 512 is prevented.

Figure 4:
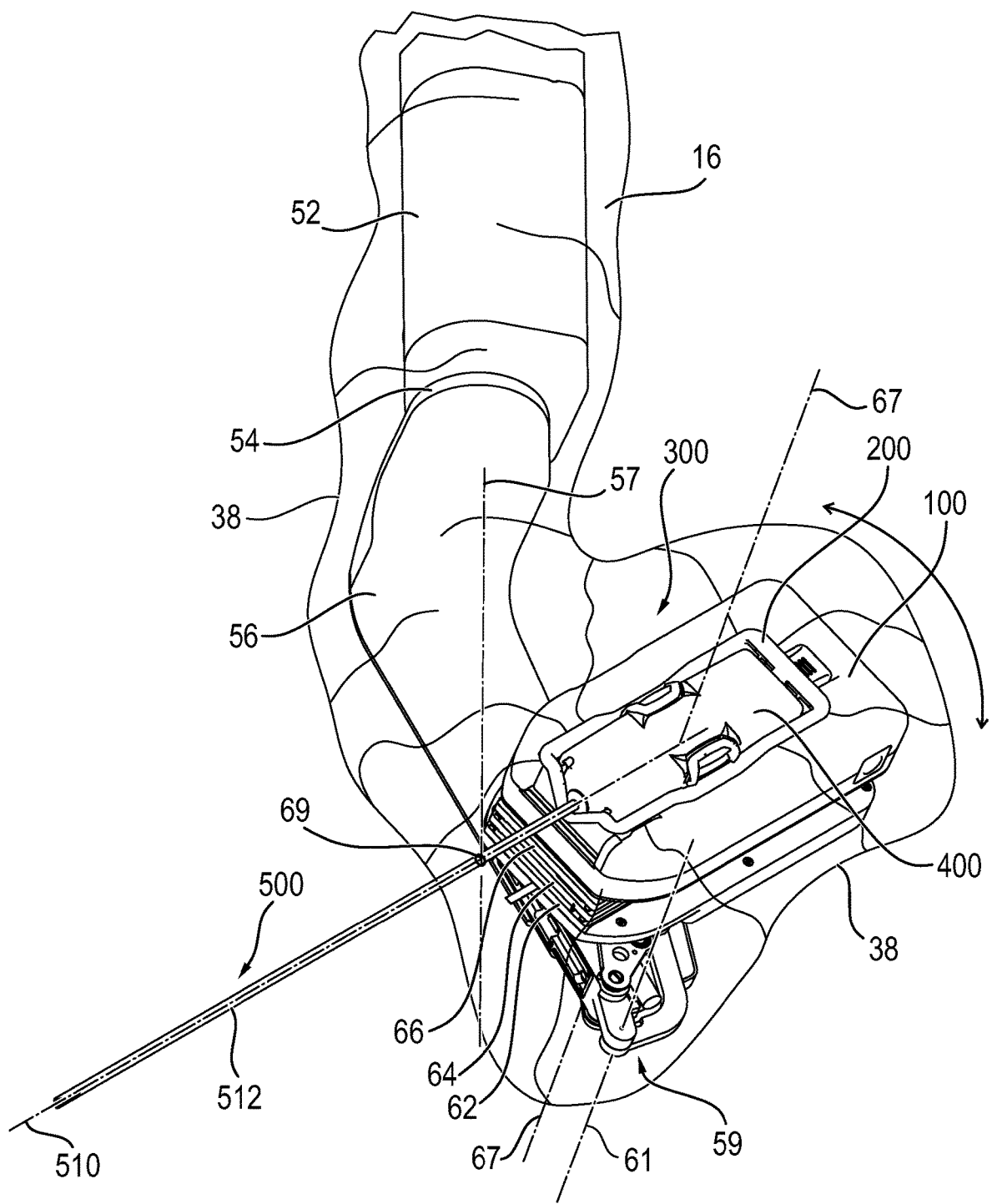
FIG. 4 shows a further perspective illustration of the arrangement according to FIG. 3.

In FIG. 4, a further perspective illustration of the arrangement according to FIG. 3 is shown, wherein the sections 62, 64, 66 of the telescopic arrangement 60 are illustrated in a retracted state in contrast to FIG. 3, as a result whereof the instrument unit 300 has been displaced in the direction of the longitudinal axis 510 of the instrument shaft 512 to the proximal end of the surgical instrument 500. Thus, by retracting the telescopic arrangement 60, the instrument unit 300 has been displaced in the direction of the proximal end of the instrument 500 along the longitudinal axis 510 of the instrument 500. In doing so, however, the position of the pivot point 69 has remained unchanged. Also given a rotation of the segments 56, 58, 60 about the axis of rotation 57, the pivot point 69 is maintained unchanged in its position in space by a corresponding drive of the drive units of the coupling gear mechanisms 59, in that a corresponding rotation of the segment 60 about the axis of rotation 61 and of the coupling unit 100 about the axis of rotation 67 takes place. Further, a virtual axis of rotation (not illustrated) which is parallel to the axes of rotation 61, 67 and orthogonal to the axis of rotation 57 and has been generated by a corresponding drive of the coupling gear mechanisms extends through the pivot point 69.

In the pivot point 69, the axis of rotation 57 of the segment 56 designed as an articulated arm and the longitudinal axis 510 of the instrument 500 intersect. The pivot point 69 is also referred to as pivotal point.

Figure 5:
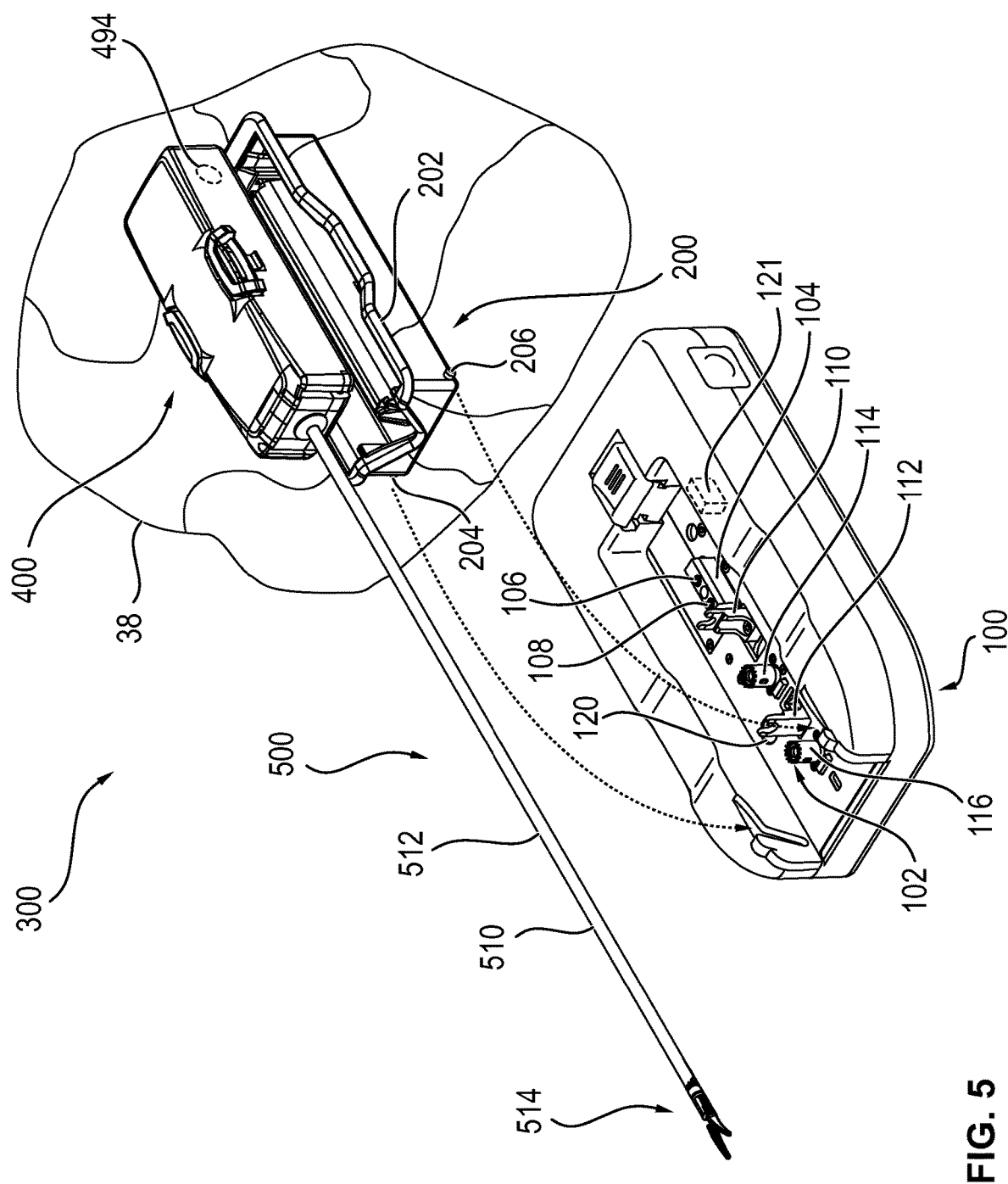
FIG. 5 shows an arrangement for connecting the instrument unit arranged in a sterile area to the non-sterile coupling unit of a manipulator arm.

FIG. 5 shows the coupling unit 100, the sterile lock 200 as well as the instrument unit 300 with the sterile unit 400 and the surgical instrument 500 having an end effector 514 prior to the connection of the sterile lock 200 to the coupling unit 100 and prior to the subsequent joining of the sterile unit 400 and the sterile lock 200. The flexible sterile cover 38 designed as a sterile foil is firmly connected to the sterile lock 200 along a circumferential connecting rim 202 of the sterile lock via a suitable connection, such as a clamping, adhesive and/or welding connection so that the sterile foil 38 forms together with the sterile lock 200 a closed sterile covering around the non-sterile elements 16, 100 to be shielded from the sterile area 39, as also shown in FIGS. 1, 3 and 4. For a better illustration, only a detail of the sterile foil 38 around the sterile lock 200 is illustrated in FIG. 5. In subsequent Figures, the sterile foil 38 is sometimes not shown.

For coupling the sterile unit 400 to the coupling unit 100 the sterile lock 200 is arranged between the sterile unit 400 and the coupling unit 100 and, in the coupled state of the sterile unit 400 to the coupling unit 100, it allows a direct coupling of a first transmitting means 102 of the coupling unit 100 and of a second transmitting means of the sterile unit 400. The second transmitting means is identified with the reference sign 406 in FIG. 11.

In the present embodiment, both mechanical energy and electrical energy is transmitted between the coupling unit 100 and the sterile unit 400 by means of the first transmitting means 102. For this, the first transmitting means 102 of the coupling unit 100 has at least four mechanical drive elements 110 to 116 and the second transmitting means 406 of the sterile unit 400 has four driven elements 412 to 418 illustrated in FIG. 11 which are complementary to the drive elements 110 to 116. Further, the first transmitting means 102 has an electrical transmitting element 104 with two electrical contacts 106, 108 and the second transmitting means 406 has an electrical transmitting element that is complementary to the electrical transmitting element 104 of the first transmitting means. The complementary electrical transmitting element comprises two electrical contacts 422, 423 illustrated in FIG. 11.

In other embodiments, the first and second transmitting means can also comprise more or less drive elements, driven elements and electrical transmitting elements, which transmit mechanical and/or electrical energy by direct coupling. As a direct coupling a coupling of the transmitting means is regarded in which no further transmitting elements are provided between the first transmitting means and the second transmitting means for a transmission of mechanical and/or electrical energy and/or optical beams, wherein in particular no electrical, mechanical or optical transmitting elements are provided in a sterile barrier, such as the sterile lock 200, arranged between the coupling unit 100 and the sterile unit 400. The coupling unit 100 further has an RFID read and write unit 121 by means of which an RFID transponder 494 of the sterile unit 400 is readable and/or writable.

Figure 6:
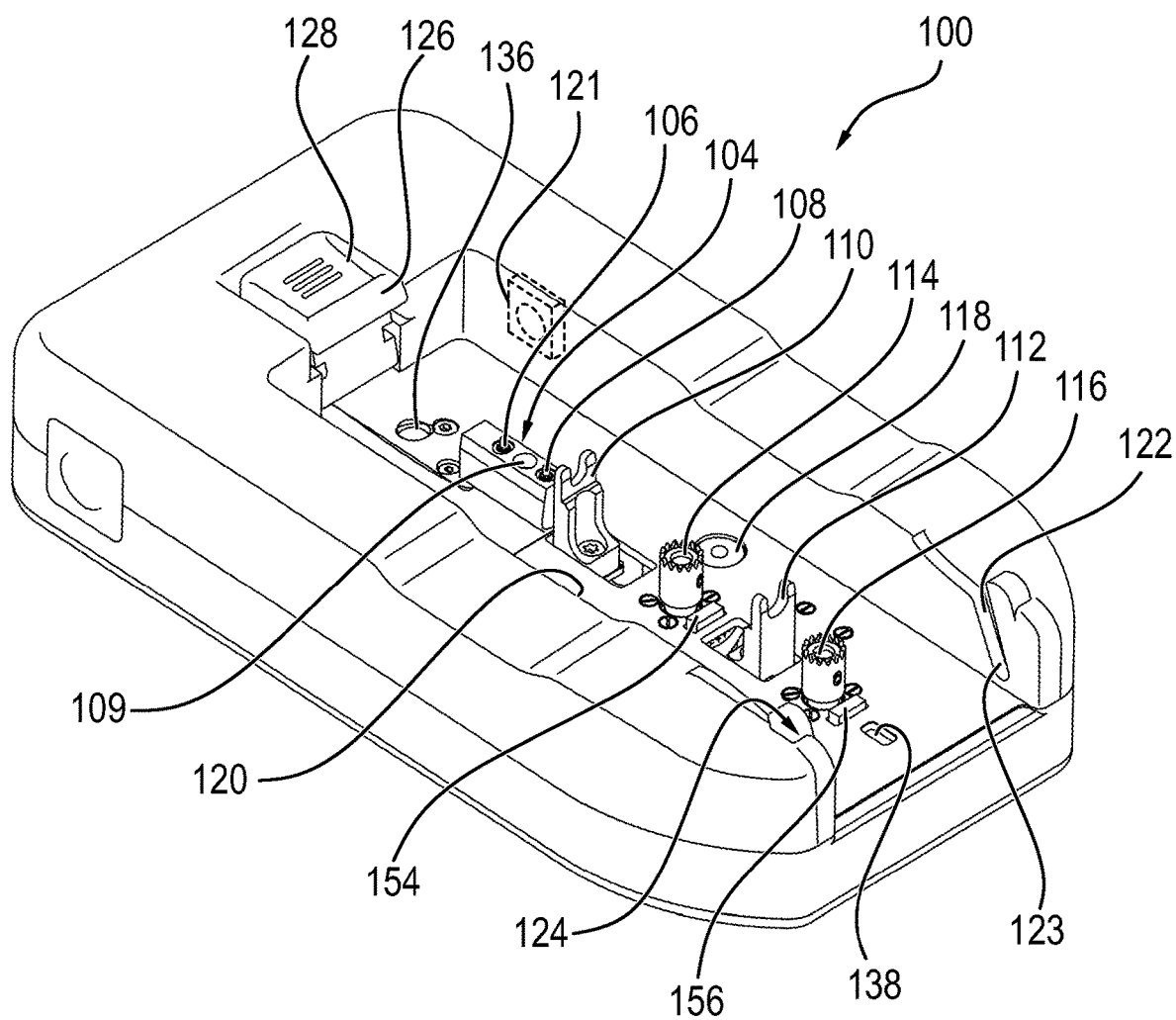
FIG. 6 shows a schematic illustration of the coupling unit of the manipulator arm.
Figure 11:
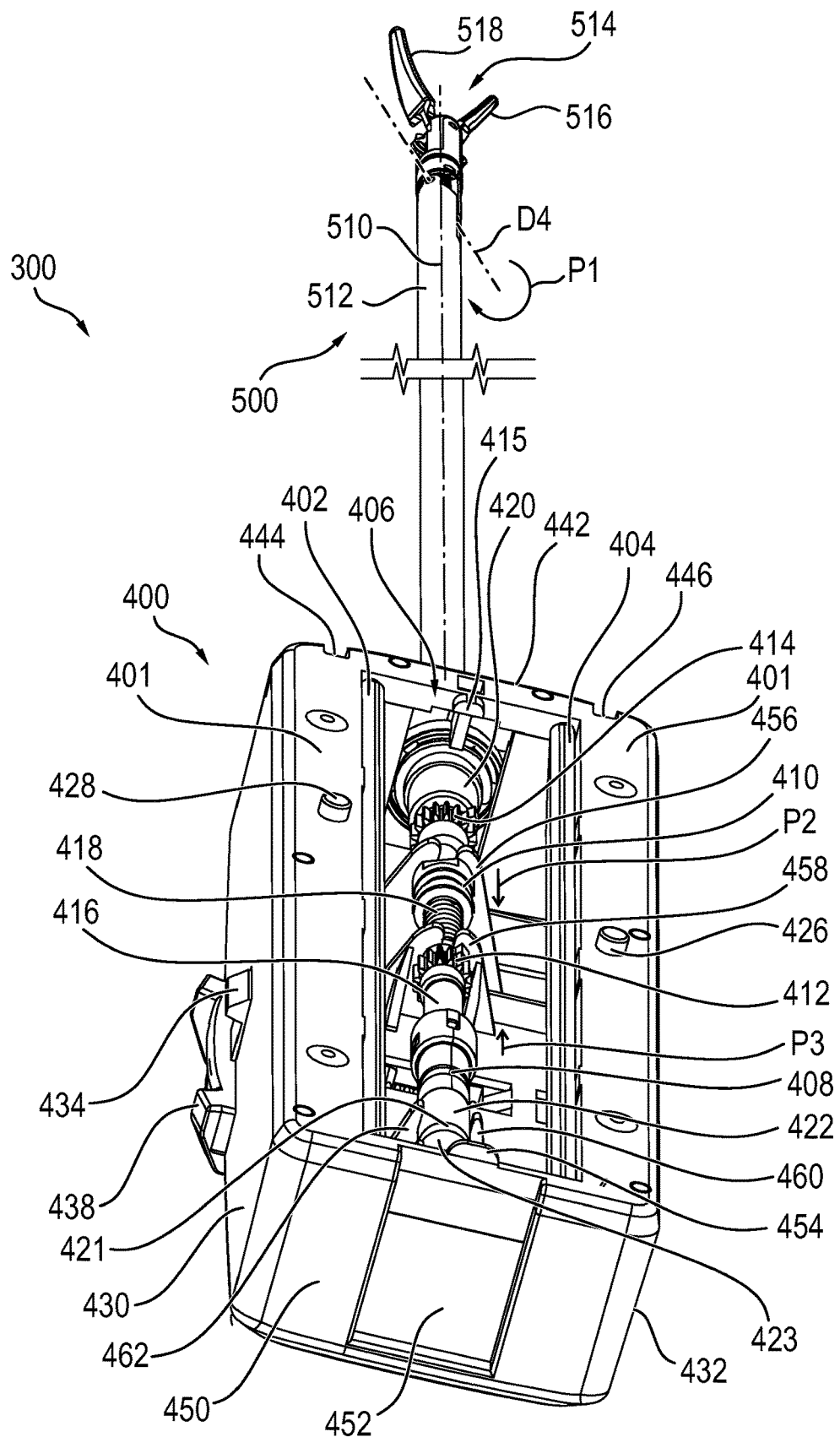
FIG. 11 shows a perspective illustration of the instrument unit with open sterile flaps of the sterile unit.

FIG. 6 shows a schematic perspective illustration of the coupling unit 100 of the manipulator arm 16. The first transmitting means 102 of the coupling unit 100 has an electrical transmitting element 104 with two electrical contacts 106, 108, an optical transmitting means 109 for transmitting light and/or optical signals, a first translatory drive element 110 and a second translatory drive element 112 each of which for transmitting a translatory movement as well as a first rotatory drive element 114 and a second rotatory drive element 116 for transmitting a rotary motion. The first and the second translatory drive element 110, 112 are each designed as a linear lift fork and the first and the second rotatory drive element 114, 116 are designed as drive pinions with end-side teeth. Further, the coupling unit 100 has a first coupling sensor 118 arranged in a recess and detecting a first detection element formed by a first detection pin projecting from the sterile unit 400 when the sterile lock 200 is correctly coupled to the coupling unit 100 and the sterile unit 400 is correctly coupled to the sterile lock 200. In this case, a first detection pin of the sterile unit 400 projects into the recess in which the first coupling sensor 118 is arranged so that it detects the presence of the first detection pin serving as a first detection element. The first detection pin is shown in FIG. 11 and is identified with the reference sign 426 therein.

Figure 10:
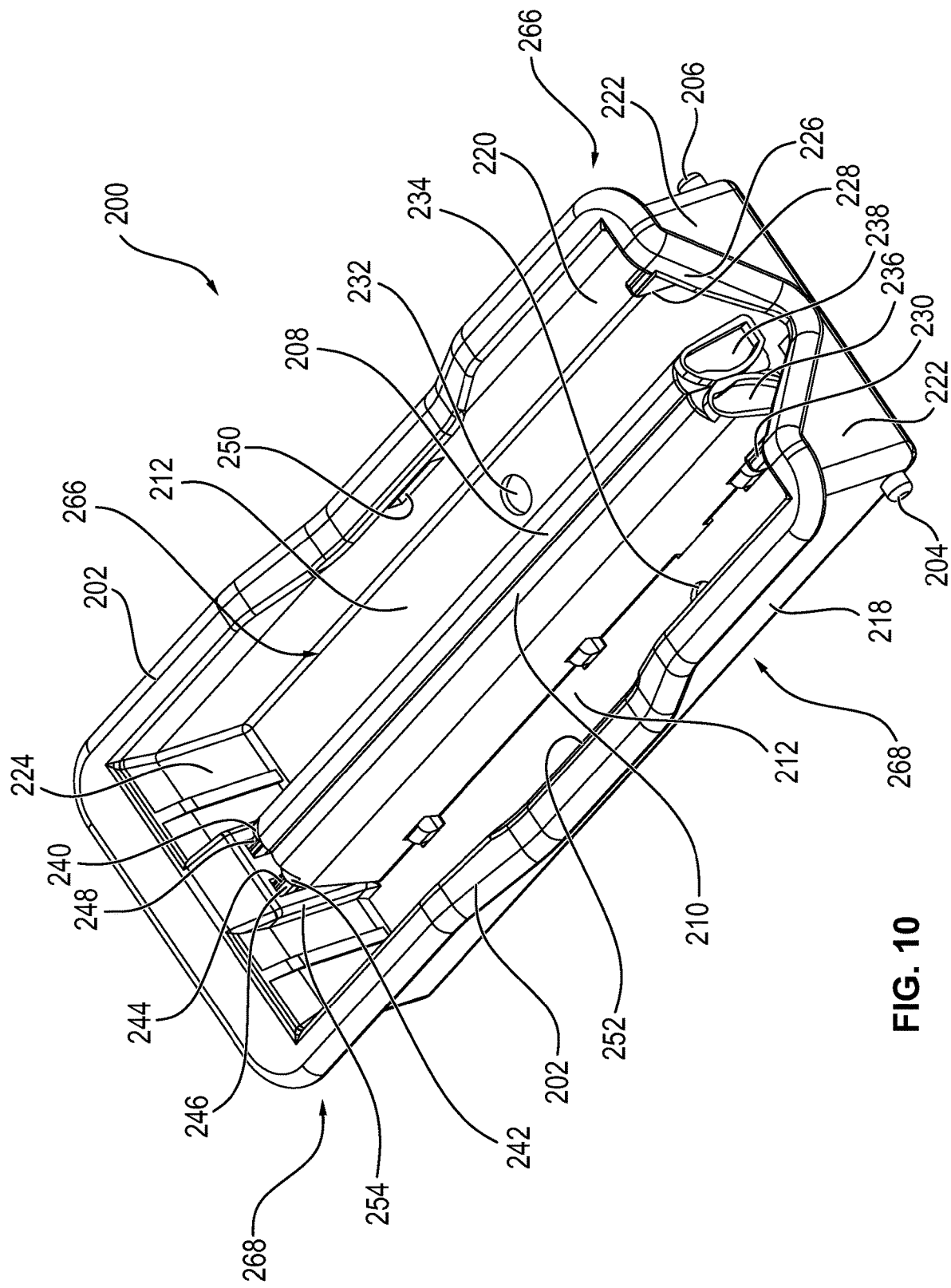
FIG. 10 shows a perspective illustration of the sterile lock with closed and locked sterile flaps.

The coupling unit 100 has a second coupling sensor 120 which is arranged laterally next to the drive elements 112, 114 in a further recess, as can be seen more clearly in FIG. 5. The second coupling sensor 120 detects a second detection element formed by a second detection pin of the sterile unit 400 when both the coupling unit 100 is correctly coupled to the sterile lock 200 and the sterile lock 200 is correctly coupled to the sterile unit 400. The second detection pin is shown in FIG. 11 and identified therein with the reference sign 428. Thus, it is reliably determined by means of the coupling sensors 118, 120 whether the sterile unit 400 is correctly coupled to the coupling unit 100 so that a direct transmission between the first transmitting means 102 of the coupling unit 100 and the second transmitting means of the sterile unit 400 is possible. For connecting the coupling unit 100 to the sterile lock 200, the coupling unit 100 has opposite guiding grooves 122, 124 into which the guiding pins 204, 206 of the sterile lock 200 are inserted until they have reached the front end 123, 125 of the respective guiding groove 122, 124, as shown in FIG. 10. At a first end of the sterile lock 200, the guiding pins 204, 206 project outward on opposite sides, as can be seen in FIGS. 5 and 10. Thereafter, the opposite second end of the sterile lock 200 is pushed downward so that the sterile lock 200 is rotated about an axis of rotation running through the guiding pins 204, 206 until a snap-in nose 126 of a snap-in element 128 engages with a complementary snap-in area of the sterile lock 200.

Figure 7:
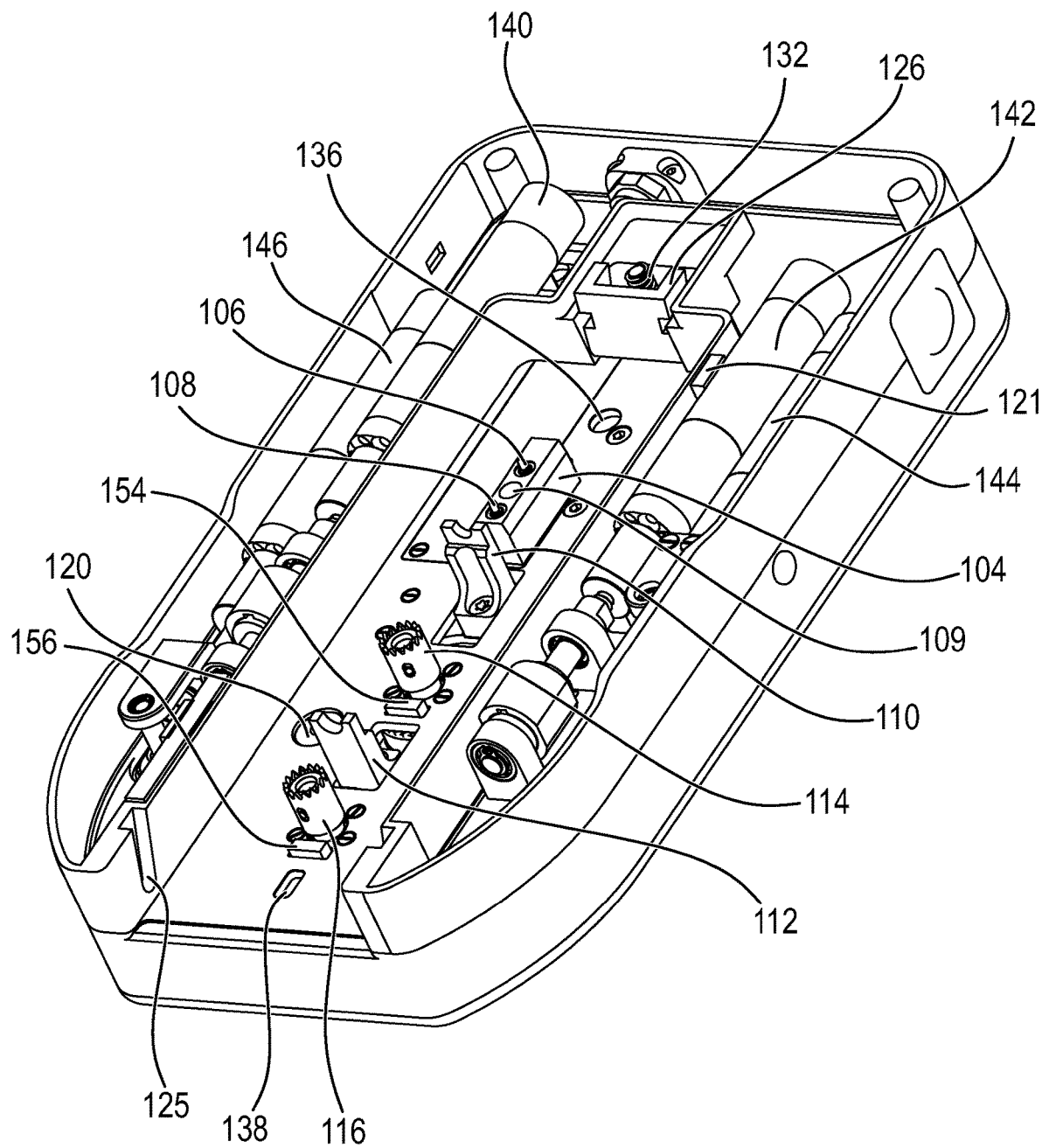
FIG. 7 shows the coupling unit according to FIG. 6 with the housing upper side being removed.
Figure 8:
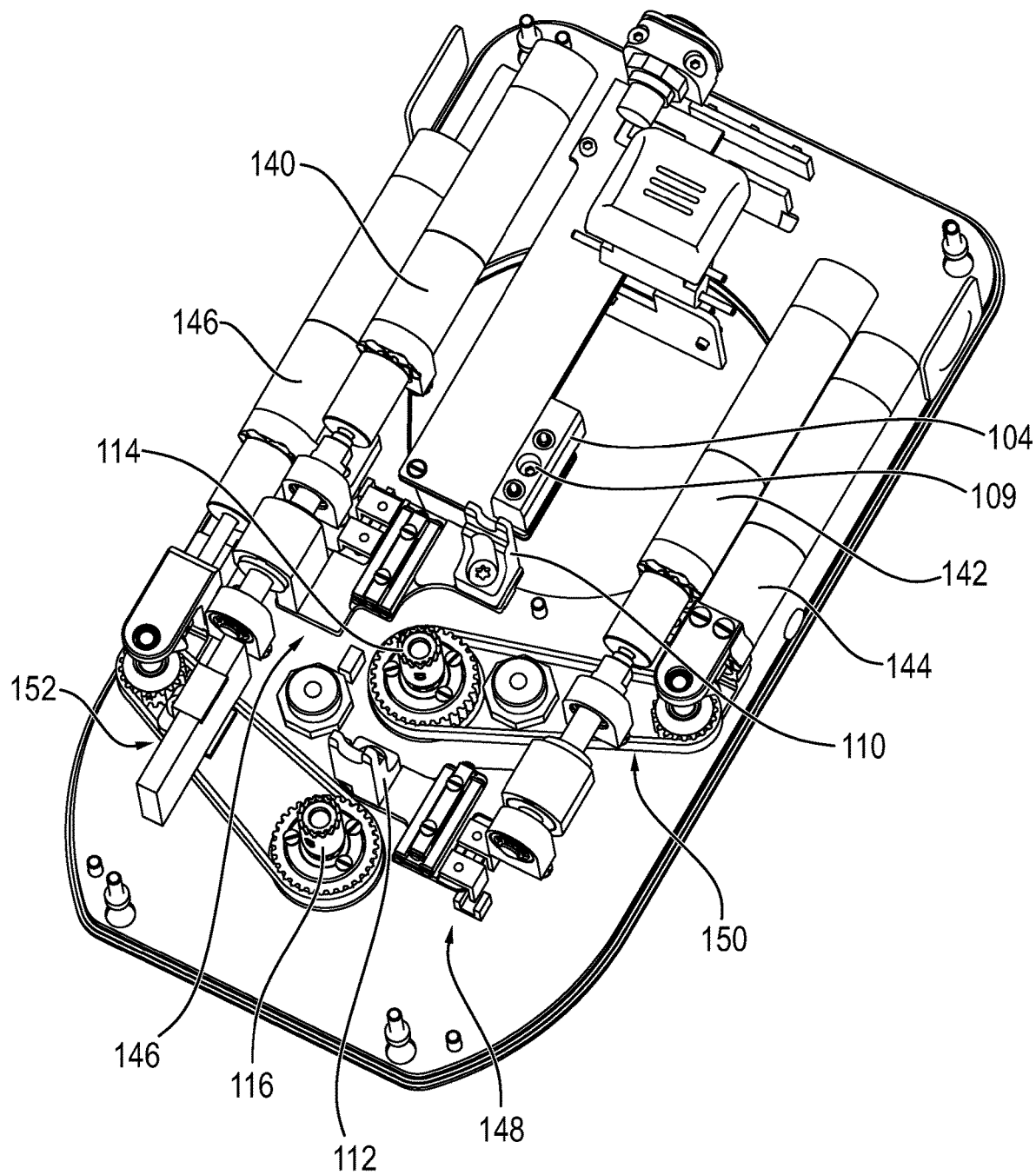
FIG. 8 shows the coupling unit according to FIGS. 6 and 7 without the upper housing segment.

FIG. 7 shows a coupling unit 100 according to FIG. 6 with the housing upper side removed and FIG. 8 shows the coupling unit 100 according to FIGS. 6 and 7 without the upper housing segment. The coupling unit 100 has altogether four drive motors 140 to 146, which are each designed as direct current motors with tachometer so that the control unit 38 is aware of the angle of rotation of the respective motor at any time and can take this into account in the further control. The first drive motor 140 is coupled via a first linear coupling gear mechanism 147 to the first translatory drive element 110 which upon an activation of the drive motor 140 by the control unit 38 performs a translatory drive movement. The second drive motor 142 is coupled via a second linear coupling gear mechanism 148 to the second translatory drive element 112 so that upon a drive movement of the second drive motor 142 the second translatory drive element 112 performs a translatory drive movement. The third drive motor 144 is coupled via a first gear stage 150 to the first rotatory drive element 114 so that upon a drive movement of the third drive motor 144 the first rotatory drive element 114 is rotated. The fourth drive motor 146 is coupled via a second gear stage 152 to the second rotatory drive element 116 so that it performs a rotary motion upon a drive movement of the fourth drive motor 146.

Figure 9:
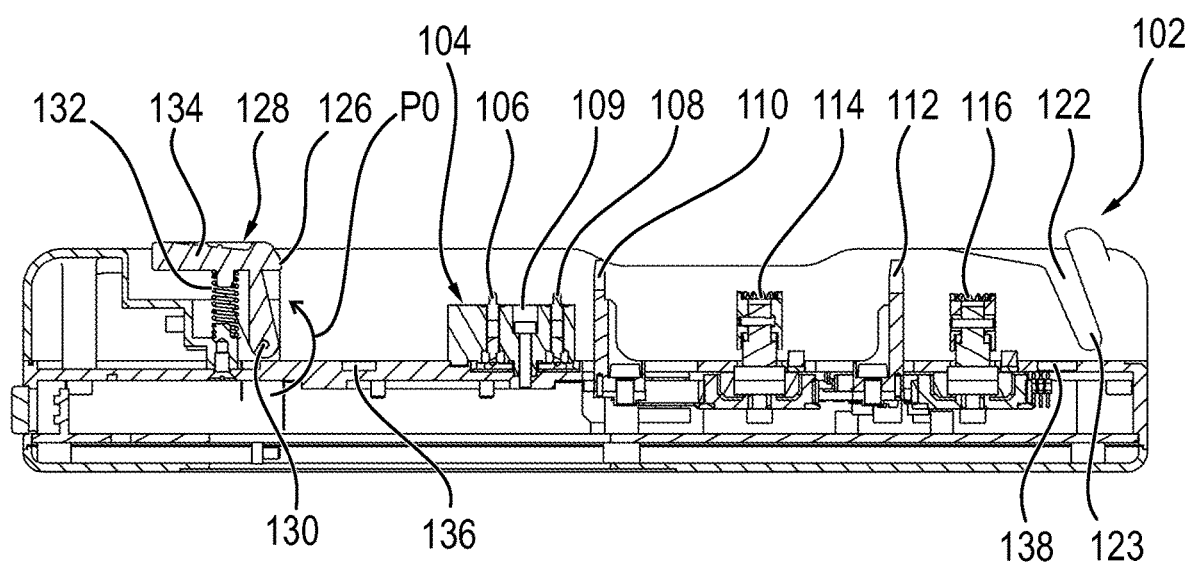
FIG. 9 shows a longitudinal section of the coupling unit according to FIGS. 6 to 8.

FIG. 9 shows a longitudinal section through the coupling unit 100. The unlocking button 128 is swivel-mounted about an axis of rotation 130 and is held in its snap-in position shown in FIG. 9 by a spring 132. For disconnecting the snap-in connection, an unlocking button 134 of the snap-in element 128 is pressed by a finger so that a spring 132 is tensioned and the snap-in element 128 together with the snap-in nose 126 is rotated in the direction of the arrow P0 so that the snap-in nose 126 is disengaged from the complementary snap-in element of the sterile lock 200. As a result, the second end of the sterile lock 200 previously engaged with the snap-in nose 126 can be pivoted out of the coupling unit 100. After this second end of the sterile lock 200 has been pivoted out of the coupling unit 100, the sterile lock 200 can be completely separated from the coupling unit 100 in that the sterile lock 200 is pulled out of the guiding grooves 122, 124 along the latter together with the guiding pins 204, 206 engaged with the guiding grooves 122, 124 until the guiding elements 204, 206 are no longer engaged with the guiding grooves 122, 124. Between the guiding grooves 122, 124 and the snap-in element 128 a receiving area formed by a corresponding recess in the housing of the coupling unit 100 is provided, which in the present embodiment surrounds the sterile lock 200 on three sides and at least in part on the bottom side.

FIG. 10 shows a perspective view of the sterile lock 200 with closed lock flaps 208, 210. The sterile lock 200 has a bottom 212 in which two openings 214, 216 are provided which can be covered by means of the lock flaps 208, 210. The lock flaps 208, 210 are pivotally connected to the bottom 212 via hinges. By means of these hinges the lock flaps 208, 210 are pivotable from the closed state shown in FIG. 10 into the open state. In the open state of the lock flaps 208, 210 a direct coupling of the drive elements 110 to 116 of the coupling unit 100 with the driven elements of the sterile unit 400 can be accomplished. Further, when the lock flaps 208, 210 are open, a direct coupling of the electrical transmitting element 104 of the coupling unit 100 to the electrical transmitting element of the sterile unit 400 can be accomplished.

The sterile lock 200 further has two side walls 218, 220, a front end wall 222 and a rear end wall 224. On the outsides of the side walls 218, 220 and the end walls 222, 224 the circumferential edge 202 is formed with which, as already described in connection with FIG. 5, the sterile foil of the sterile cover 38 is connected in a suitable manner.

On the inside of the front end wall 222 two guiding and unlocking webs 228, 230 are firmly arranged on each side next to a V-shaped recess 226 of the end wall 222, which webs serve as unlocking elements for unlocking the sterile flaps of the sterile unit 400 when the sterile lock 200 is connected to the sterile unit 400.

In the bottom 212 of the sterile lock 200, a first detection window 232 and a second detection window 234, each in the form of a through hole, are provided, through which the already mentioned detection elements 426, 428 of the sterile unit 400 are passed so that they can be detected by the first coupling sensor 118 and by the second coupling sensor 120 of the coupling unit 100.

At the front and rear end of the lock flaps 208, 210, one guiding bead 236 to 242 each is provided. The front guiding beads 236, 238 have no function. In the closed state of the lock flaps 208, 210, the tines 246, 248 of a guiding fork 244 engage with the rear guiding beads 240, 242. The guiding fork 244 is pushed into its upper position shown in FIG. 10 by means of a spring and closes the lock flaps 208, 210 by way of engagement of its tines 246, 248 into the guiding beads 240, 242 and keeps them in their closed position. As a result of the engagement of the fork tines 246, 248, the lock flaps 208, 210 cannot be pushed apart so that the non-sterile transmitting means 102 of the coupling unit 100 is reliably covered when the lock flaps 208, 210 are closed and the non-sterile elements of the coupling unit 100 are reliably shielded from the sterile area 39.

In the side walls 218, 220, one snap-in bead 250, 252 each is provided into which a snap-in element of the sterile unit 400 engages when the sterile lock 200 is connected to the sterile unit 400. At the rear end wall 224 of the sterile lock 200 a guiding web 254 is provided which engages into a guiding groove 452 of the sterile unit 400 when the sterile lock 200 is connected to the sterile unit 400, as shown in FIG. 11.

On the outside of the rear end wall 224 of the sterile lock 200 a snap-in nose is formed into which the snap-in nose 126 of the snap-in element 128 of the coupling unit 100 engages when the coupling unit 100 is connected to the sterile lock 200.

As can be seen from FIG. 10, the side walls 218, 220, the end walls 222, 224 and the bottom 218 form a housing trough into which the sterile unit 400 is insertable at least in part for connecting the sterile unit 400 to the coupling unit 100. The housing trough thus generally serves as a first connecting area 266 of the sterile lock 200. The outside of the sterile lock 200 serves as a second connecting area 268 with which the sterile lock 200 is connectable to the coupling unit 100.

FIG. 11 shows a perspective illustration of the instrument unit 300 with the sterile unit 400 and the surgical instrument 500. At the proximal end of the rotatable outer instrument shaft 512 the bendable and rotatable end effector 514 with actuatable gripping arms 516, 518 is arranged. The movements of the end effector 514 can be performed by means of the drive elements 110 to 116 of the coupling unit 100 and the driven elements 408 to 414 of the sterile unit 400 when the sterile unit 400 is connected to the coupling unit 100 via the sterile lock 200. The sterile unit 400 has sterile flaps 402, 404, which are shown in an open state in FIG. 11 and in a closed state in FIG. 12. Inside the sterile unit 400, the second transmitting means is arranged which is visible when the sterile flaps 402, 404 are open and is identified with the reference sign 406. When coupled to the coupling unit, the second transmitting means 406 comprises a first translationally driven element 408 engaged with the first translatory drive element 110 and a second translationally driven element 410 engaged with the second translatory drive element 112 of the coupling unit 100, each time for transmitting a translation. Further, a first rotationally driven element 412 couplable to the first rotary drive element 114 of the coupling unit 100 as well as a second rotationally driven element 414 engaged with the second rotary drive element 116 of the coupling unit 100 are provided for transmitting a rotary motion each. In the surgical instrument 500 connected to the coupling unit 400, the end effector 514 is pivoted about the tilt axis D4 in the arrow direction P1 by up to 90° when the second translationally driven element 410 of the sterile unit 400 is moved by the second translatory drive element 112 of the coupling unit 100 in the direction of the arrow P2. When moving the first translationally driven element 408 in the direction of the arrow P3, the gripping arms 516, 518 of the end effector 514 are moved apart and moved towards each other in opposite directions. When driving the first rotationally driven element 412 of the sterile unit 400 with the aid of the first rotary drive element 114 of the coupling unit 100 the end effector 514 can be rotated independent of the instrument shaft 512. By means of the second rotationally driven element 414, given a coupling and a drive by means of the second rotary drive element 116 of the coupling unit 100, a rotation of the instrument shaft 512 about its longitudinal axis 510 can be produced to rotate the position of the tilt axis D4 of the end effector 514 about the axis of rotation 510 of the outer instrument shaft 512 without the end effector 514 itself being rotated.

Further, a first spring 416 is provided which pushes the first translationally driven element 408 of the sterile unit 400 opposite to the direction of the arrow P3 into its end position. Further, a second spring 418 is provided which pushes the second translationally driven element 410 of the sterile unit 400 opposite to the direction of the arrow P2 into its end position. Further, the sterile unit 400 has a bearing 420 for rotatably mounting the outer instrument shaft 512 in the sterile unit 400. As an alternative to the surgical instrument 500, also other instruments, such as a pair of scissors, a needle holder, optical instruments, rinsing units, aspiration units, instruments of high-frequency surgery and other instruments used in operations, in particular in laparoscopic surgeries can be coupled to the sterile unit 400, wherein the second transmitting means 406 are designed for the implementation of the corresponding functions.

According to the embodiment, the second transmitting means 406 further comprises an electrical transmitting element with a first electrical contact 422 designed as a slip ring and a second electrical contact 423 designed as a slip ring, which, when coupling the sterile unit 400 to the coupling unit 100 via the sterile lock 200, establish an electrical connection with the electrical contacts 106, 108 of the coupling unit 100 for transmitting high-frequency electrical energy for high-frequency surgery. In other embodiments, also no electrical transmitting means may be provided.

The sterile unit 400 has two projecting cams 415, 417 which upon insertion of the sterile unit 400 into the sterile lock 200 push the unlocked sterile flaps 208, 210 apart at least until the cams 415, 417 are arranged between the sterile flaps 208, 210. Upon further insertion of the sterile unit 400 into the sterile lock 200, wedge-shaped engaging elements 456 to 462 of the sterile unit 400 push the sterile flaps 208, 210 further apart until they are arranged in their open position shown in FIG. 18.

Figure 12:
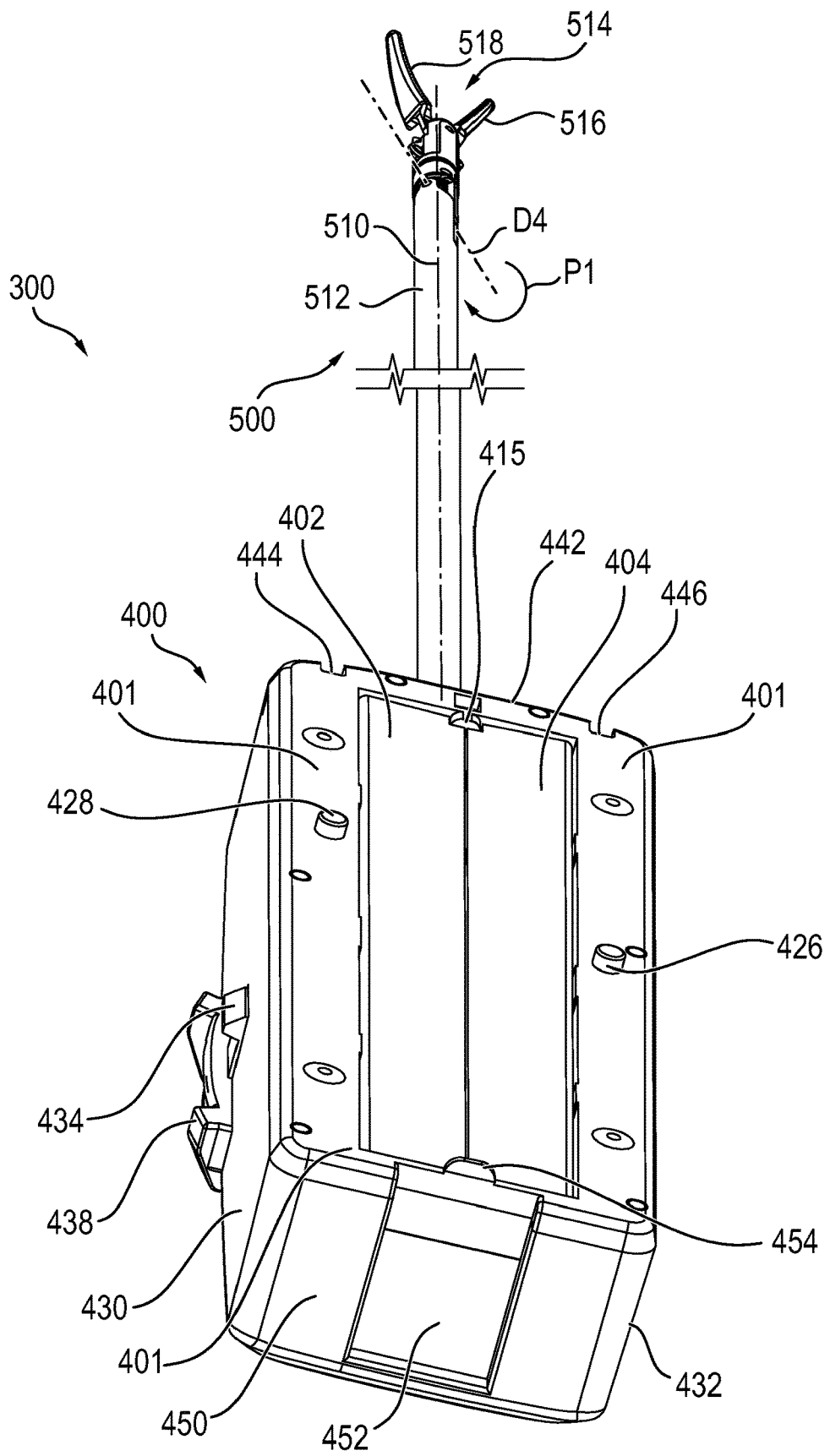
FIG. 12 shows a perspective illustration of the instrument unit according to FIG. 11 with closed sterile flaps.

The bottom plate 401 of the sterile unit 400 facing upward in FIGS. 11 and 12 has, as already mentioned, two detection elements 426, 428 formed as projecting detection pins. When coupling the sterile unit 400 to the coupling unit 100 with the sterile lock 200 arranged between the sterile unit 400 and the coupling unit 100, the detection element 426 projects through the first detection window 232 of the sterile lock 200 into the recess of the first coupling sensor 118 of the coupling unit 100 and the second detection element 428 projects through the second detection window 234 into the recess of the second coupling sensor 120 of the coupling unit 100. When the detections elements 426, 428 are detected by means of the coupling sensors 118, 120, a correct coupling of the sterile lock 200 to the coupling unit 100 and of the sterile unit 400 to the sterile lock 200 can be detected so that only after a detection of the detection elements 426, 428 with the aid of the coupling sensors 118, 120 a drive of the transmitting elements 110 to 116 is released by a control unit. Further, the transmission of high-frequency energy is only released after the correct detection of the detection elements 426, 428 by means of the coupling sensors 118, 120 via the transmitting elements 106, 108.

Further, the sterile unit 400 has two snap-in elements 434, 436 arranged on opposite side walls 430, 432, which snap-in elements are actuatable by means of an actuating element 438, 440 projecting from the side wall 430, 432. The snap-in elements 434, 436 engage with the snap-in beads 250, 252 provided in the side walls 218, 220 of the sterile lock 200 when the sterile unit 400 is correctly connected to the sterile lock 200.

The front end wall 442 of the sterile unit 400 has two grooves 444, 446 into which the guiding and unlocking webs 228, 230 of the sterile lock 200 are inserted when the sterile unit 400 is connected to the sterile lock 200 and, in doing so, unlock the sterile flaps 402, 404.

Further, the guiding web 254 of the sterile lock 200 engages into the guiding groove 452 present on the rear end side 450 of the sterile unit 400. At the lower end of the guiding groove 452, an actuating bar 454 projects outward from the bottom plate 401 and pushes the guiding fork 244 downward when the sterile unit 400 is inserted into the sterile lock 200 and thus releases the lock of the lock flaps 208, 210 by the guiding fork 244.

Figure 13:
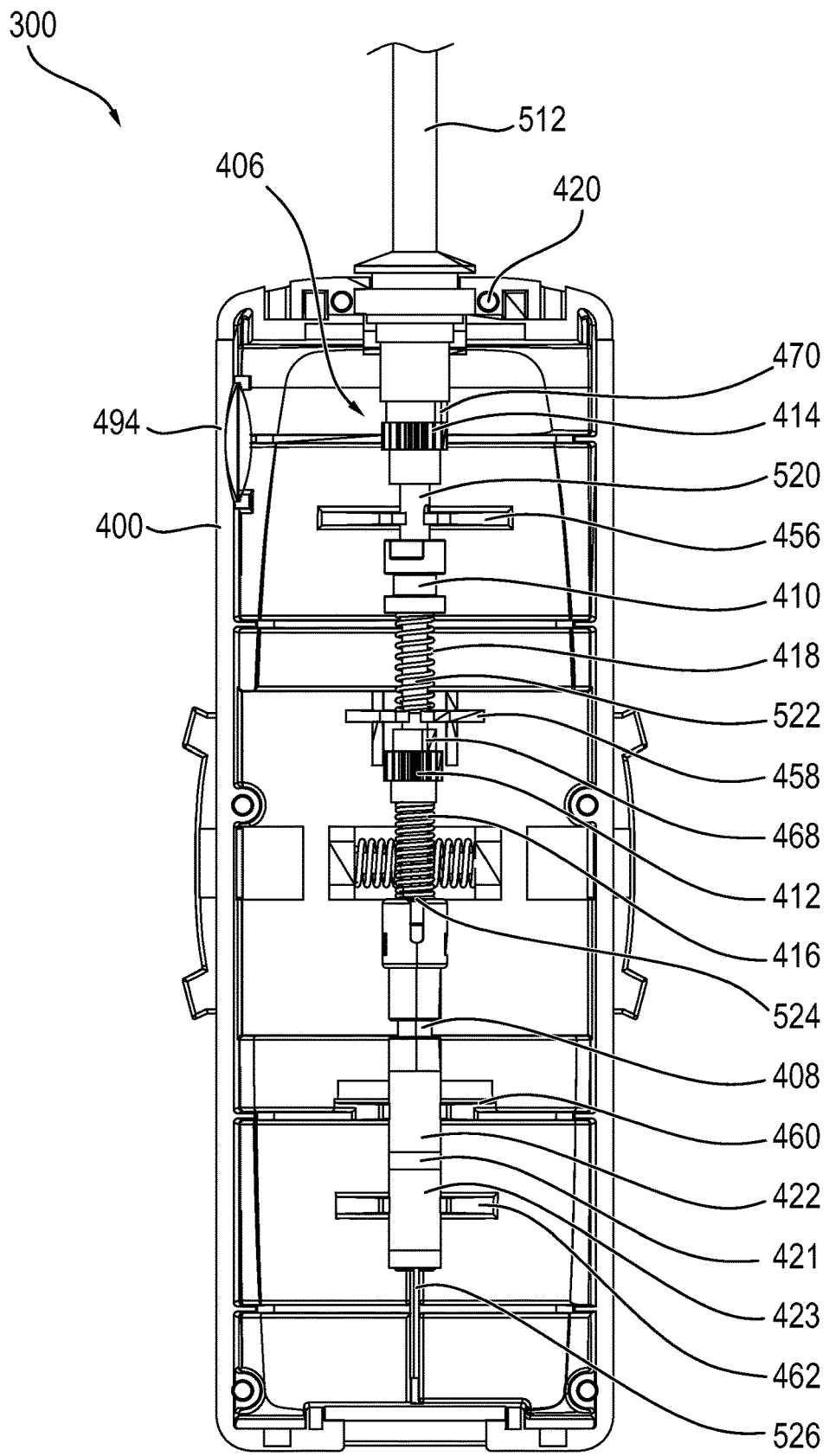
FIG. 13 shows the instrument unit according to FIGS. 11 and 12 with removed bottom plate.
Figure 14:
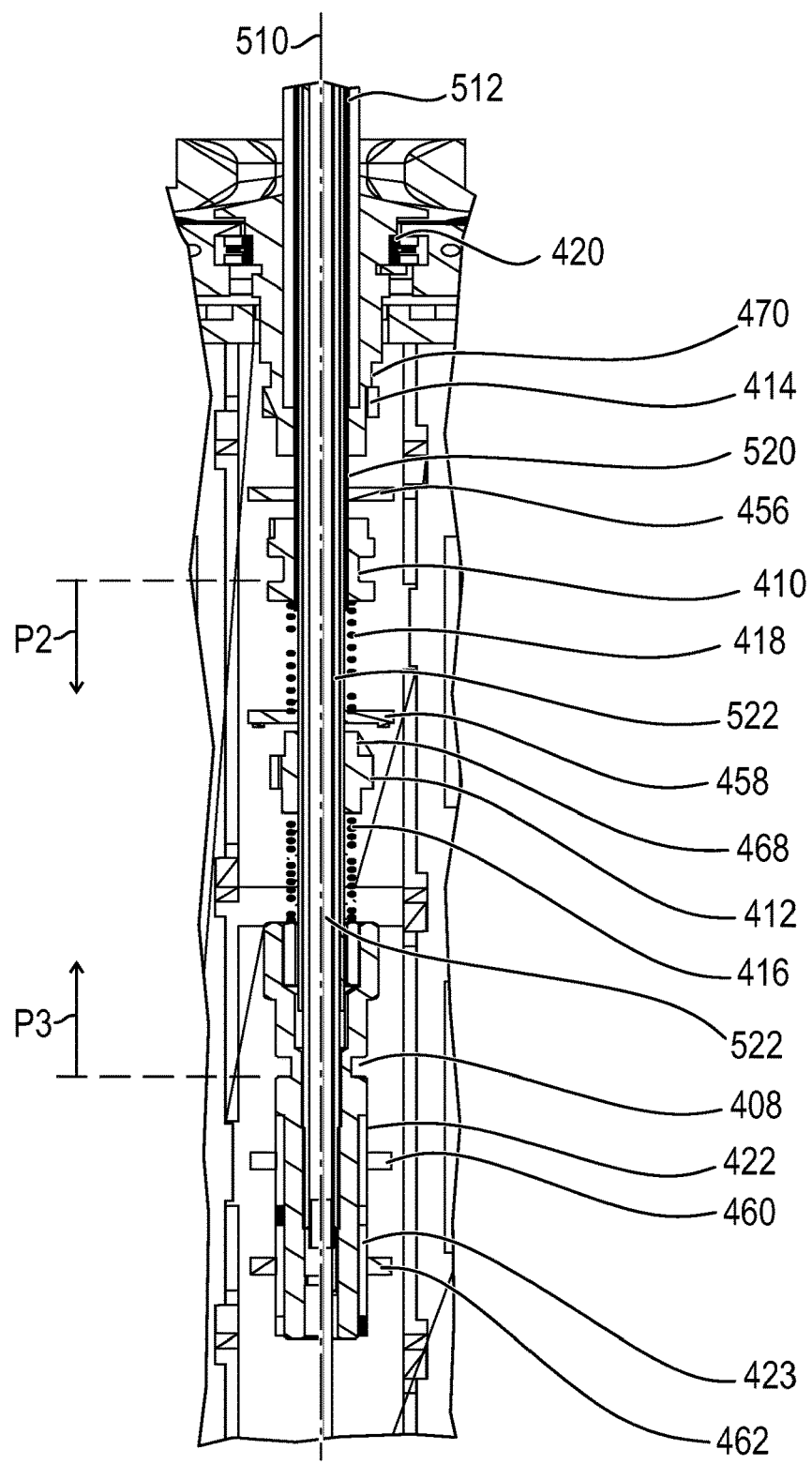
FIG. 14 shows a sectional illustration of a detail of the instrument unit according to FIG. 13 with several elements drivable by means of drive elements of the coupling unit.

FIG. 13 shows the instrument unit 300 according to FIGS. 11 and 12, wherein the bottom plate 401 of the sterile unit 400 has been removed. FIG. 14 shows a sectional view of a detail of the instrument unit 300 according to FIG. 13 with several elements 408 to 414 driven by means of the drive elements 110 to 116 of the coupling unit 100. The second rotationally driven element 414 formed as a gearwheel is connected in a rotationally fixed manner to the outer instrument shaft 512 and a second angle transmitter 470 for detecting the shaft rotation of the outer instrument shaft 512. The second angle transmitter 470 has a projecting cam at one position along its circumference, which cam can be detected by means of a second position sensor 156 of the coupling unit 100 when the cam is arranged opposite to the second position sensor 156.

The second translationally driven element 410 is connected to a first inner instrument shaft 520 so that given a translational movement of the second translationally driven element 410 the first inner instrument shaft 520 is moved translationally.

The first rotationally driven element 412 is connected in a rotationally fixed manner to a first angle transmitter 468 and a second inner instrument shaft 522. In the same manner as the second angle transmitter 470, the first angle transmitter 468 has a projecting cam at one position along its circumference, which cam is detectable by means of a first position sensor 154 of the coupling unit 100 when the cam is arranged opposite to this first position sensor 154. The second inner instrument shaft 522 serves for end effector rotation independent of the rotary angle of the outer instrument shaft 512. The first inner instrument shaft 520 serves to bend the end effector 514.

The first translationally driven element 408 is connected to a third inner instrument shaft 524 for transmitting a translational drive movement. The third inner instrument shaft 524 in particular serve to perform a jaw part movement of the gripping arms 516, 518 of the end effector 514, which are in particular illustrated in FIG. 11.

In the case of an initialization directly after coupling the sterile unit 400 to the coupling unit 100, a rotation of the rotationally driven elements 412, 414 together with the angle transmitters 468, 470 by maximally 360° is performed each time, as a result whereof the exact initial rotary position of the outer instrument shaft 512 or the second inner instrument shaft 522 is determined and set, based on which the control unit 38 determines the exact rotary position of the respective instrument shaft 512, 522 and continuously monitors it by means of the tachogenerator assigned to the respective drive motor 144, 146 so that the exact rotary angle position of the respective instrument shaft 512, 522 is known to the control unit 38 at any time and can be taken into account in the further control of the drive motors 140 to 146.

Between the electrical contacts 422 and 423 designed as slip rings there is an optical interface 421 which also serves to mutually electrically insulate the electrical contacts 422, 423. The electrical contacts 422, 423 are connected to cables which are guided in the third inner instrument shaft 524 to the gripping arms 516, 518 of the end effector 514.

If required, further cables and/or optical fibers can be passed through the third inner instrument shaft 524 to the end effector 514.

In the sectional view illustrated in FIG. 14, the coaxial arrangement of the outer instrument shaft 512 and of the inner instrument shafts 520 to 526 is well visible. The V-shaped elements 456 to 462 serves as mounting webs for mounting the inner shafts 520 to 526, wherein the inner shafts 520 to 526 are mounted directly or indirectly rotatably in the mounting webs 520 to 526.

Figure 15:
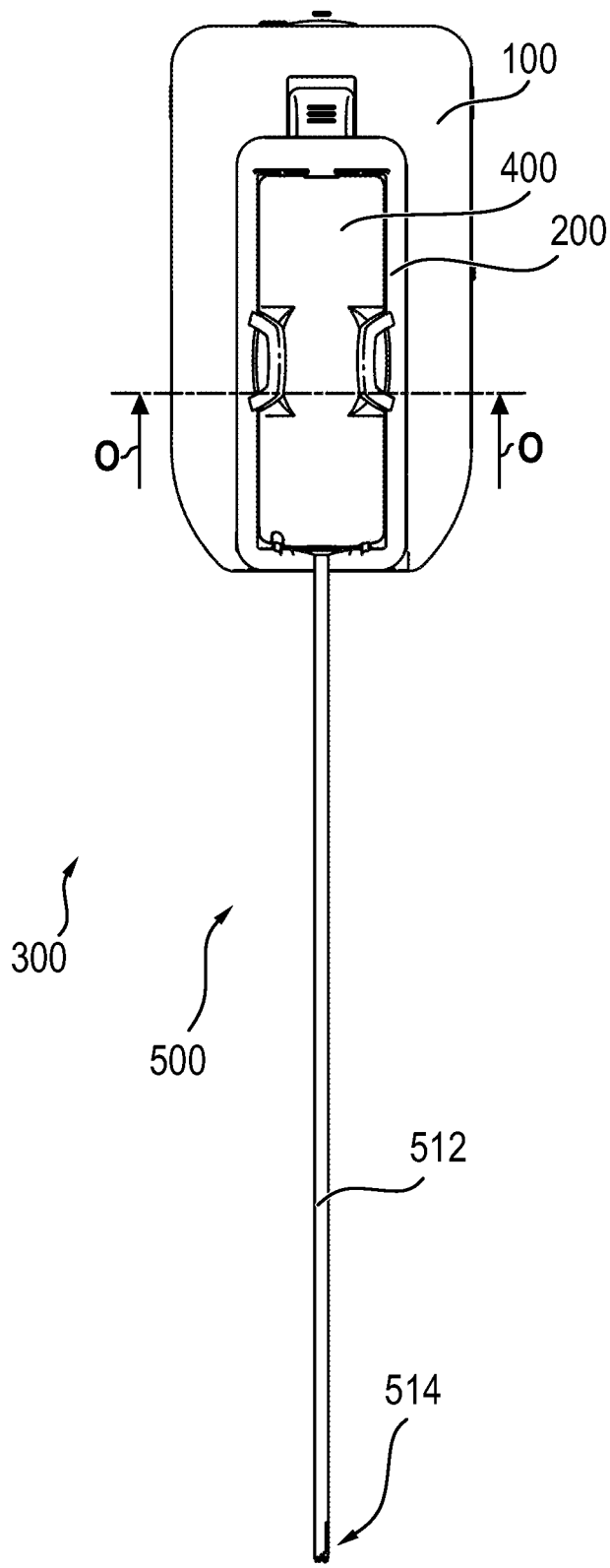
FIG. 15 shows a top view of an arrangement of the coupling unit, sterile lock and instrument unit.
Figure 16:
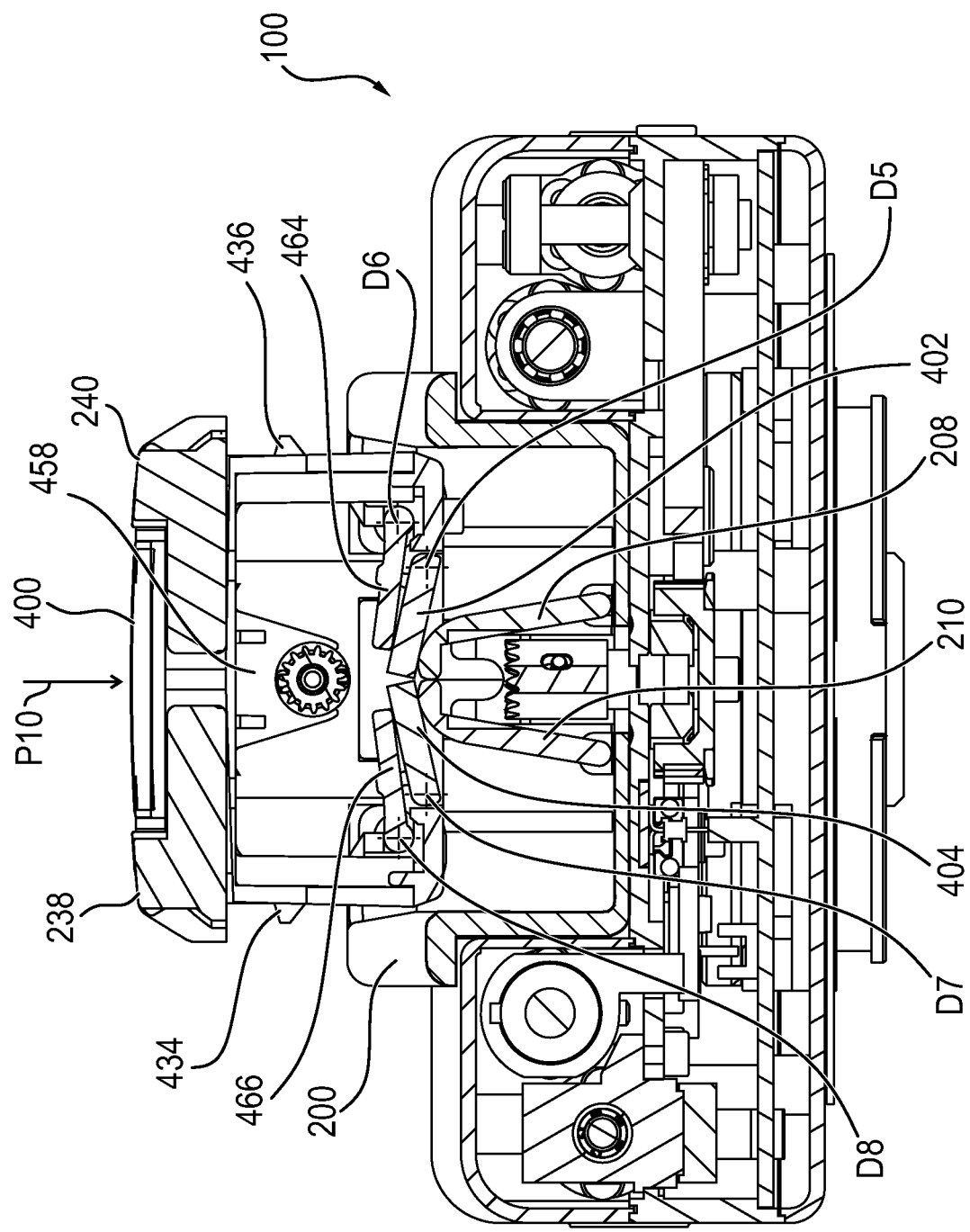
FIG. 16 shows a sectional view of the arrangement according to FIG. 15 along the sectional line O-O in a first position for connecting the instrument unit to the sterile lock coupled to the coupling unit.
Figure 17:
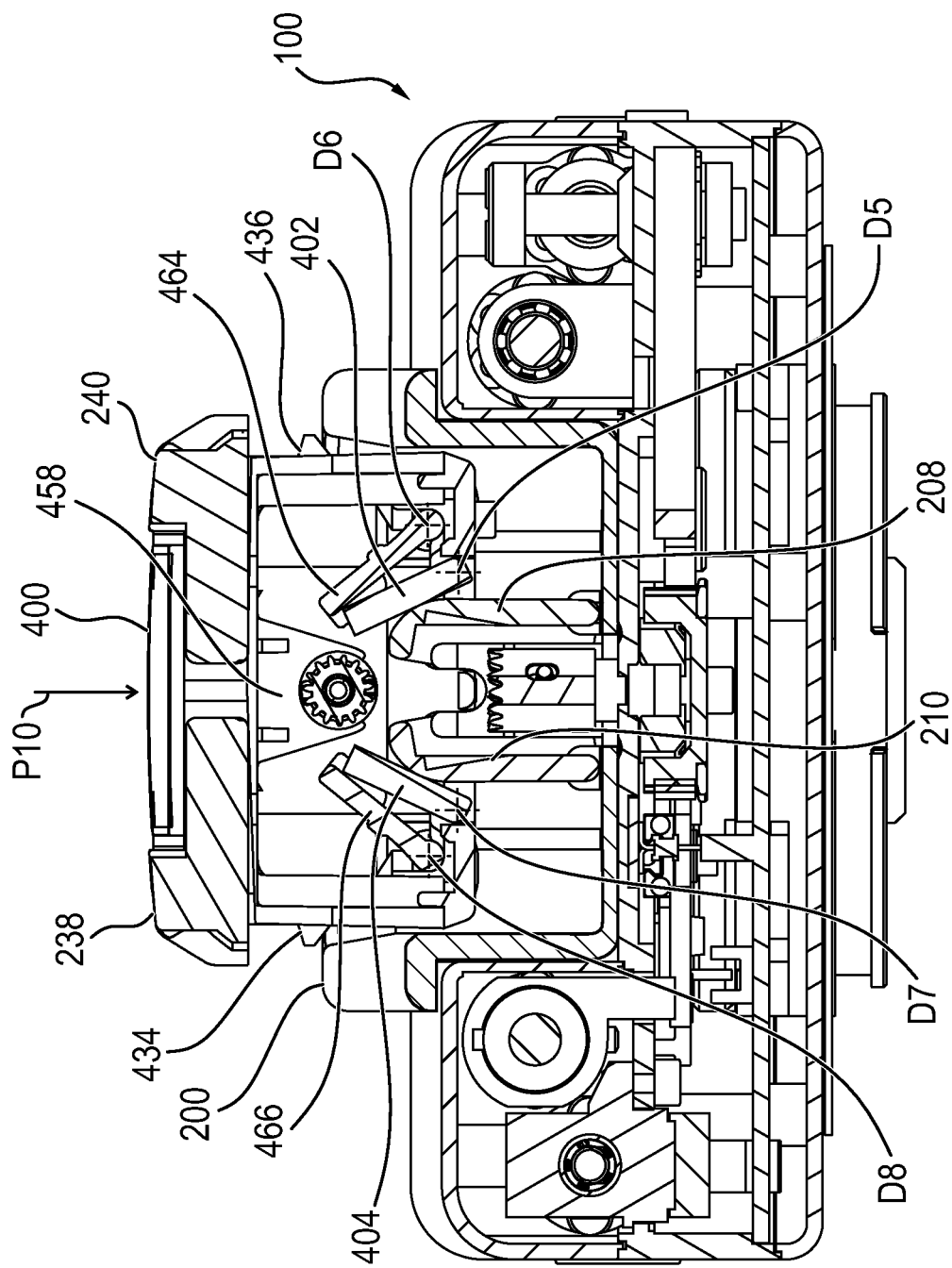
FIG. 17 shows a sectional view of the arrangement according to FIG. 15 along the sectional line O-O in a second position for connecting the instrument unit to the sterile lock coupled to the coupling unit.
Figure 18:
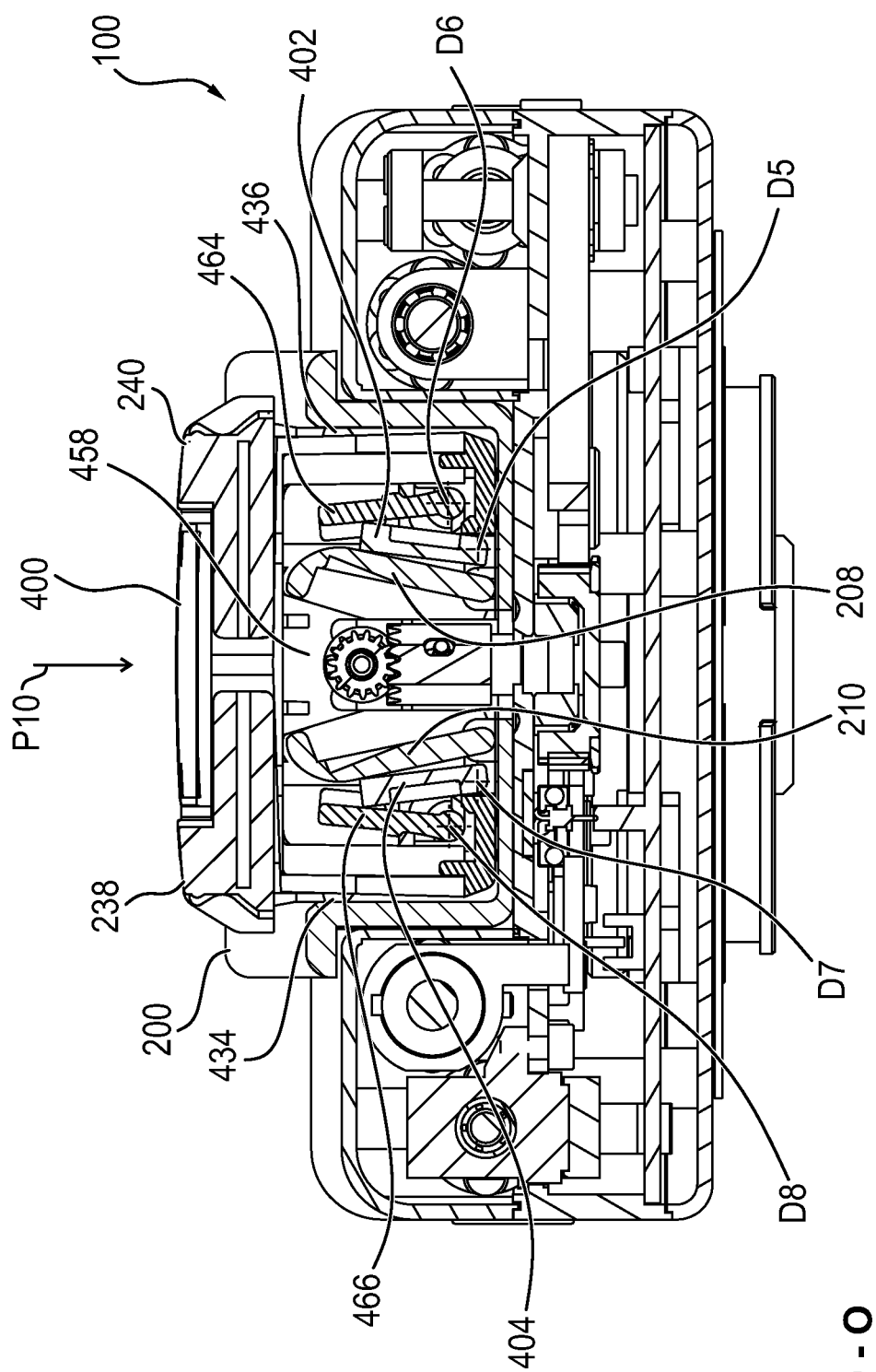
FIG. 18 shows a sectional view of the arrangement according to FIG. 15 along the sectional line O-O in a third position for connecting the instrument unit to the sterile lock coupled to the coupling unit.

FIG. 15 shows a top view of an arrangement with the coupling unit 100, the sterile lock 200 and the instrument unit 300 comprising the sterile unit 400 and the sterile surgical instrument 500. FIG. 16 shows a sectional illustration of the arrangement according to FIG. 15 along the sectional line O-O in a first position immediately before connecting the sterile unit 400 of the instrument unit 300 to the sterile lock 200 already coupled to the coupling unit 100. FIG. 17 shows a sectional illustration of the arrangement according to FIG. 15 along the sectional line O-O in a second position for connecting the sterile unit 400 of the instrument unit 300 to the sterile lock 200 already coupled to the coupling unit 100. FIG. 18 shows a sectional illustration of the arrangement according to FIG. 15 along the sectional line O-O in a third position in which the sterile unit 400 of the instrument unit 300 is connected to the sterile lock 200 coupled to the coupling unit 100 so that the first transmitting means 102 of the coupling unit are engaged with the transmitting elements of the second transmitting means 406 for direct coupling. In the position shown in FIG. 16, the guiding flaps 464, 466 have been moved by the insertion of the guiding and unlocking webs 228, 230 into the grooves 444, 446 and thus have already been moved along their axis of rotation D6, D8 in the direction of the arrows P4, P5 from their locked position into their unlocked position so that the sterile flaps 402, 404 together with the guiding flaps 464, 466 have been pushed open by a movement of the sterile unit 400 in the direction of the arrow P10 and the contact of the sterile flaps 402, 404 with the lock flaps 208, 210 caused thereby. As a result, the sterile unit 400 gets deeper into the receiving area of the sterile lock 200 provided for receiving the sterile unit 400 so that the actuating web 454 comes into engagement with the guiding fork 244 and pivots the same against the spring force of the guiding fork spring. As a result, the tines 246, 248 of the guiding fork 244 are engaged with the guiding beads 240, 242 such that the lock flaps 208, 210 can be pushed apart by the cams 415, 417 and thus be opened. When the sterile unit 400 is further moved in the direction of the arrow P10, the V-shaped engaging elements 458 to 462 come into engagement with the lock flaps 208, 210 and push these and the sterile flaps 402, 404 together with the guiding flaps 464, 466 further outward into their fully open position shown in FIG. 18. By the contact of the lock flaps 208, 210 with the sterile flaps 402, 404, these are opened further together with the guiding flaps 464, 466 until all flaps 208, 210, 402, 404, 464, 466 are arranged in the open position shown in FIG. 18. Upon a reversed movement of the sterile unit 400, when the sterile unit 400 is removed from the sterile lock 200, i.e. from the position shown in FIG. 18 into the position shown in FIG. 16 opposite to the direction of the arrow P10, a reversed sequence of motion of the sterile, guiding and lock flaps takes place so that these flaps are in particular closed by the spring force of the springs and the tines 246, 248 of the guiding fork 244 are again engaged with the guiding beads 240, 242 and completely close the lock flaps 208, 210. By the positive connection between the fork tines 246, 248 and the guiding beads 240, 244 caused in this way, the lock flaps 208, 210 are reliably held in their closed position so that the lock flaps 208, 210 cannot be opened from outside. Further, the guiding flaps 464, 466 are completely closed and moved into their locked position by means of the springs when the sterile unit 400 is removed from the sterile lock 200 so that afterwards these cannot be opened even when an external force is applied on the sterile flaps 402, 404.

Figure 19:
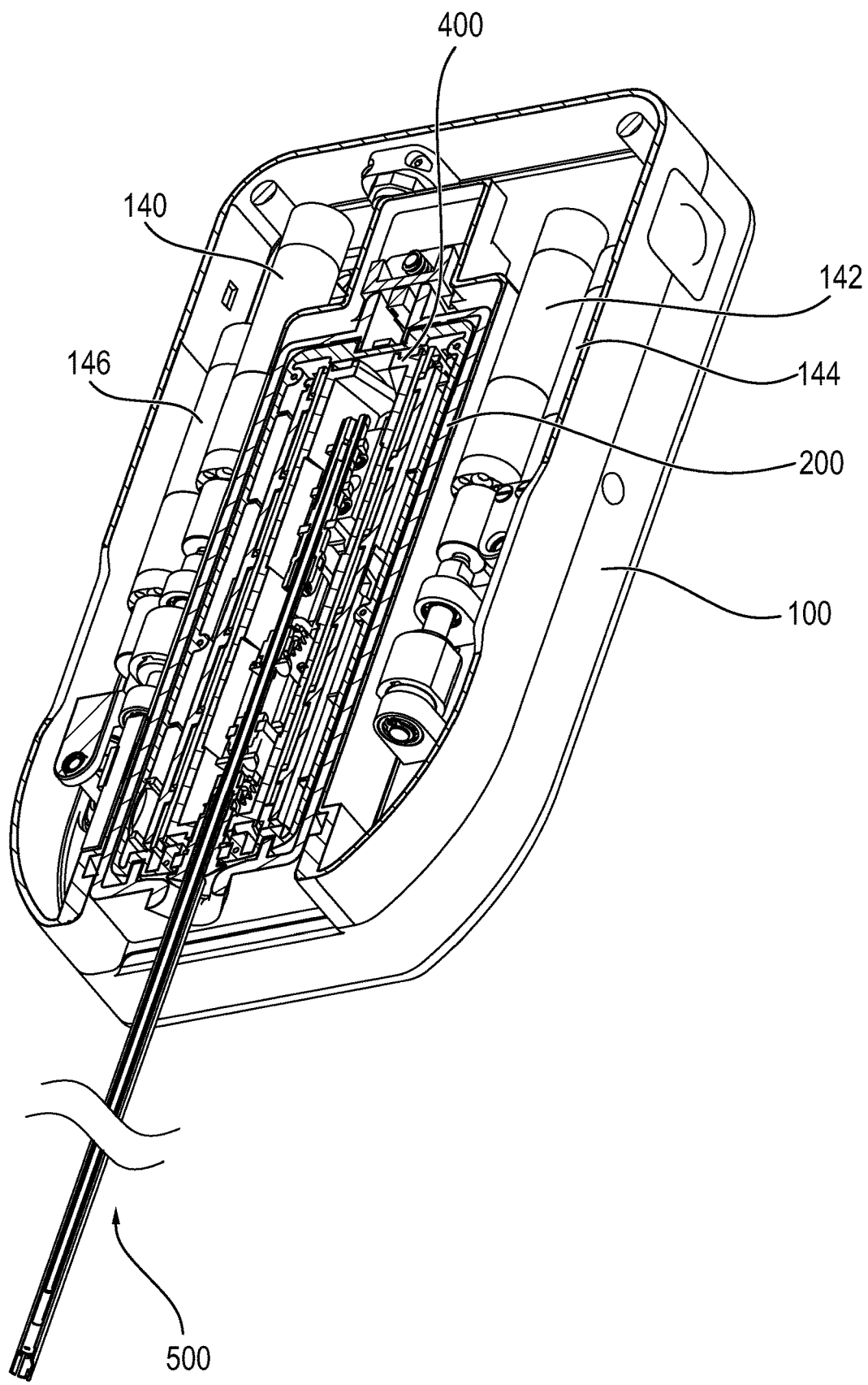
FIG. 19 shows a sectional illustration of the instrument unit, sterile lock and coupling unit in the connected state.

FIG. 19 shows a sectional illustration of the instrument unit 300 of the sterile lock 200 and of the coupling unit 100 in the connected state. Here, from the coupling unit 100 and from the sterile unit 400 and the sterile lock 200 the upper housing parts have been cut off so that the arrangement of the sterile lock 200 within the receiving area of the coupling unit 100 and the arrangement of the sterile unit 400 within the receiving area of the sterile lock 200 are well visible.

Figure 20:
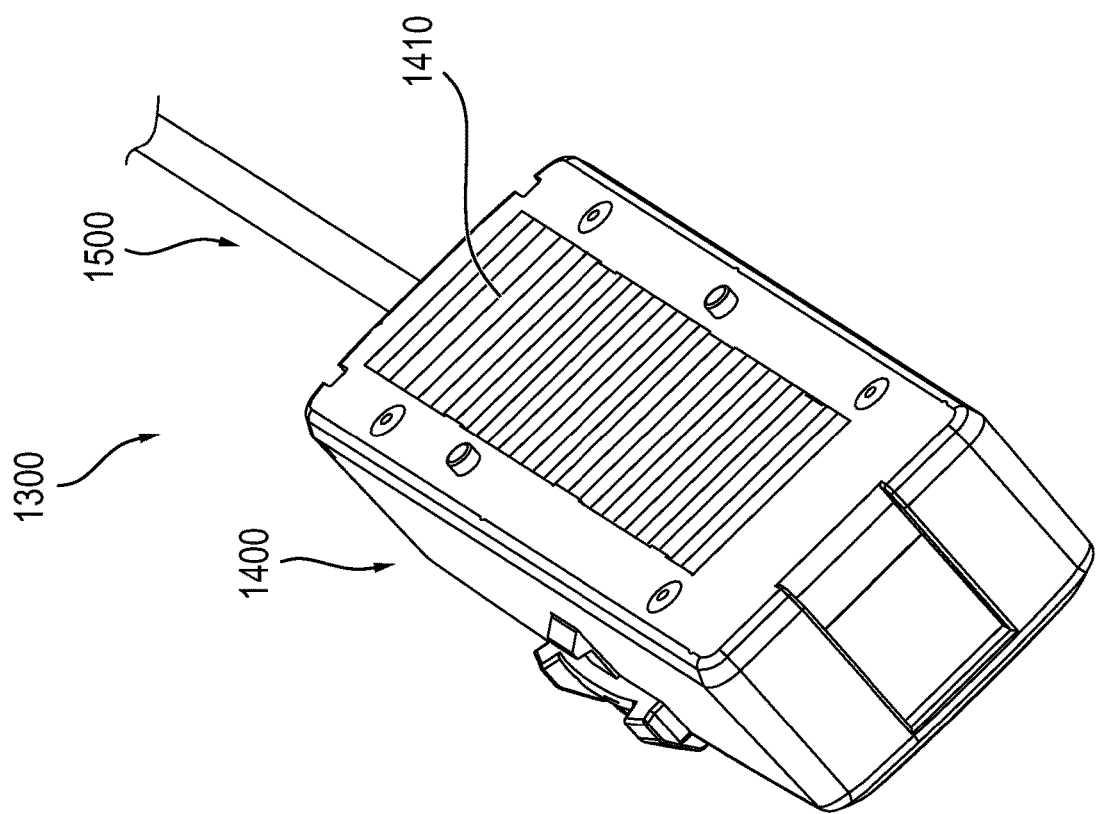
FIG. 20 shows a detail of an instrument unit according to a second embodiment.

FIG. 20 shows a detail of an instrument unit 1300 with a sterile unit 1400 and a surgical instrument 1500 according to a second embodiment. In contrast to the instrument unit 300, the sterile unit 1400 of the instrument unit 1300 has no sterile flaps but a jalousie 1410 for covering the driven elements in a sterile manner. The further structure and the function of the instrument unit 1300 corresponds to the structure and the function of the instrument unit 300 according to FIGS. 1 to 19.

Figure 21:
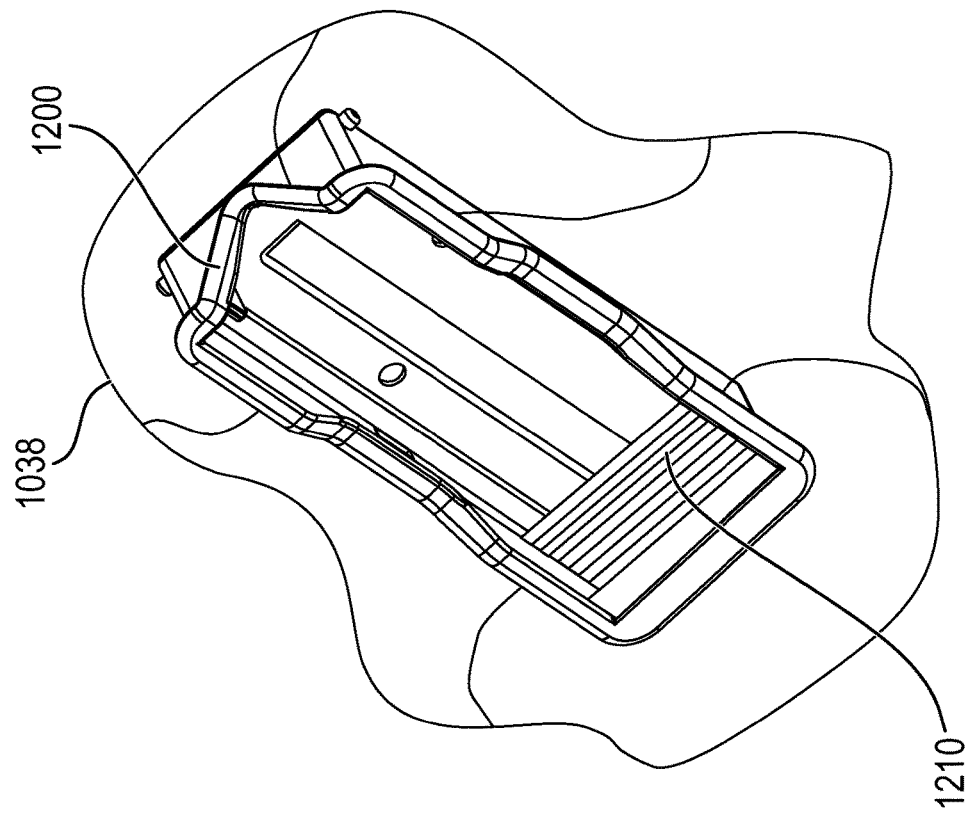
FIG. 21 shows a sterile cover with a sterile lock according to a second embodiment.

FIG. 21 shows a detail of a sterile covering 1038 with a sterile lock 1200 which in contrast to the sterile lock 200 has no sterile flaps but a jalousie 1210 for shielding drive elements of the coupling unit 100 in a sterile manner. The jalousie 1410 of the coupling unit 1400 and the jalousie 1210 of the sterile lock 1200 are opened in a suitable manner by a mechanical engagement when connecting the sterile unit 1400 to the sterile lock 1200 or the sterile unit 1400 to the sterile lock 200 or the sterile unit 400 to the sterile lock 1200, respectively. Alternatively, active drive elements, such as one electric motor each, for opening and closing the respective jalousie 1410, 1210 can be provided.

Figure 22:
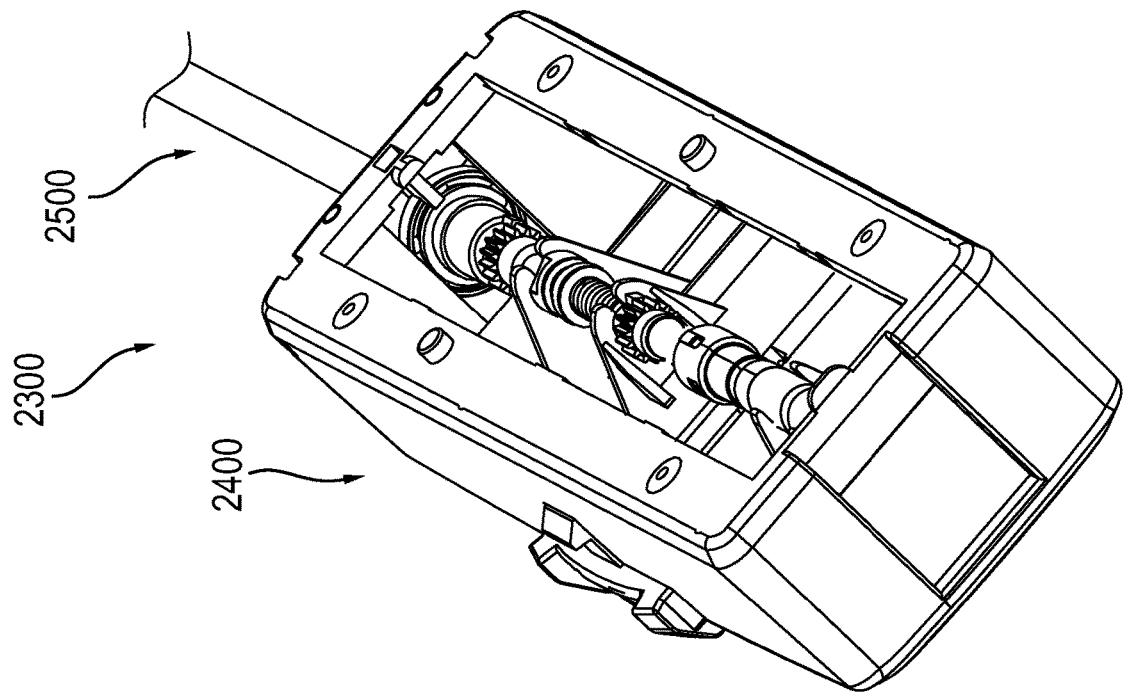
FIG. 22 shows a detail of an instrument unit according to a third embodiment.

In FIG. 22, a detail of an instrument unit 2300 with a sterile unit 2400 according to a third embodiment is shown. The sterile unit 2400 has no elements for covering the driven elements in a sterile manner so that this instrument unit 2400 is immediately removed from the sterile area 39 after separation from the sterile lock 200, 1200 or after separation from a further sterile lock 2200 shown in FIG. 23.

Figure 23:
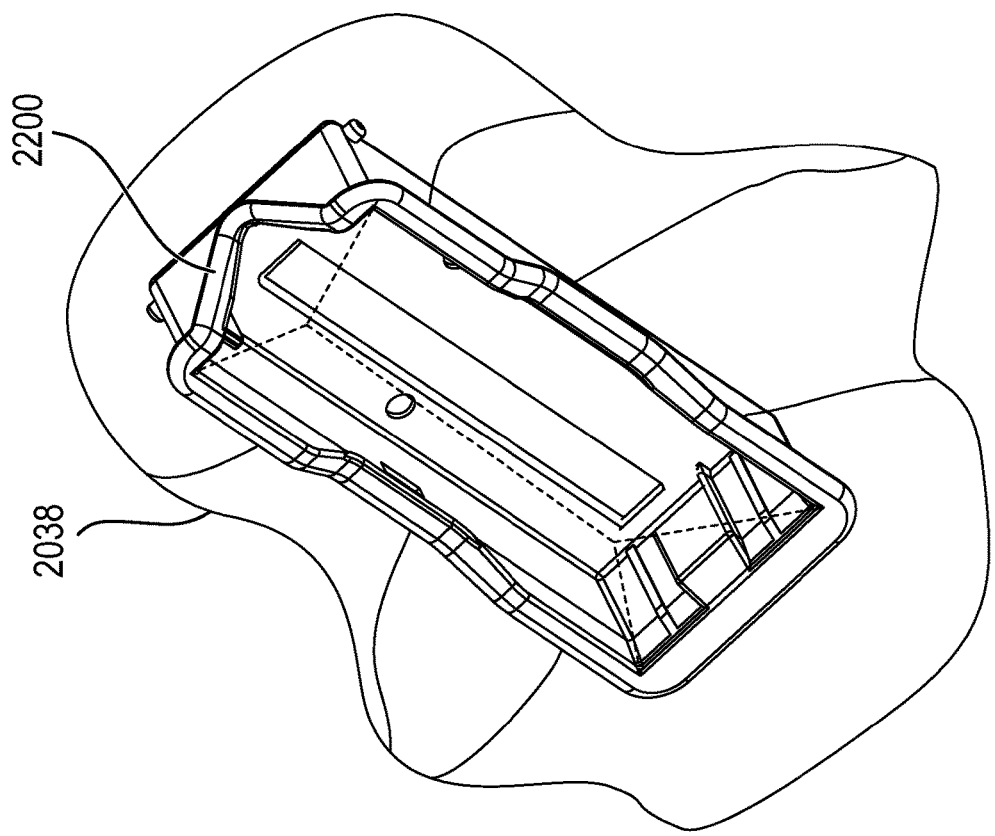
FIG. 23 shows a sterile cover with a sterile lock according to a third embodiment.

The sterile cover 2038 shown in FIG. 23 comprises a sterile lock 2200 which is couplable to the coupling unit 100 just like the sterile unit 200. In contrast to the sterile lock 200, the sterile lock 2200 has no lock flaps but comprises a foil provided with predetermined breaking points indicated by means of dotted lines, which foil is torn open along the predetermined breaking points when connecting a sterile unit 400, 1400, 2400 to the sterile lock 2200 so that a direct coupling of the drive elements 110 to 116 of the coupling unit 100 with the driven elements 408 to 414 is easily possible. Preferably, when using the sterile lock 2200, the sterile unit 400, 1400, 2400 is not separated during a surgery but only after the surgery has been terminated.

This application claims priority to German patent application No. 10 2014 117 408.9 filed Nov. 27, 2014 which is hereby incorporated by reference in its entirety.

The invention claimed is:

1. A device for robot-assisted surgery, comprising
at least one non-sterile manipulator arm having a coupling unit with drive elements,
a sterile instrument unit arranged in a sterile area and comprising a surgical instrument and a sterile unit for coupling the surgical instrument to the drive elements of the coupling unit,
a sterile cover for shielding at least a part of the manipulator arm from the sterile area, wherein
the coupling unit comprises a translatory drive element for generating a translatory drive movement and a rotatory drive element for generating a rotatory drive movement,
the sterile unit has a translationally driven element engaged with the translatory drive element so that the translationally driven element is translationally driven by the translatory drive element, and a rotationally driven element engaged with the rotatory drive element so that the rotationally driven element is rotationally driven by the rotatory drive element,
that the sterile cover comprises a sterile lock which is connectable to the coupling unit and to the sterile unit,
that the sterile lock connected to the coupling unit shields the translatory drive element and the rotatory drive element in a sterile manner before the sterile unit is connected to the sterile lock and after the sterile unit has been separated from the sterile lock.

2. The device according to claim 1, wherein the sterile lock connected to the coupling unit and to the sterile unit provides access to the drive elements such that the translatory drive element is couplable to the translationally driven element and the rotatory drive element is couplable to the rotationally driven element.

3. The device according to claim 1, wherein the sterile unit comprises a sterile cover which shields the driven elements in a sterile manner before the sterile unit is connected to the sterile lock and after the sterile unit has been separated from the sterile lock and that the sterile unit provides access to the driven elements when the sterile lock is connected to the coupling unit and to the sterile unit.

4. The device according to claim 3, wherein the sterile cover that shields the driven elements in a sterile manner comprises:
a flap.

5. The device according to claim 1, wherein the sterile lock comprises a sterile cover which shields the drive elements of the coupling unit in a sterile manner before the sterile unit is connected to the sterile lock and after the sterile unit has been separated from the sterile lock, and that the sterile lock provides access to the drive elements when the sterile lock is connected to the coupling unit and to the sterile unit.

6. The device according to claim 1, wherein the translatory drive element of the coupling unit is a first translatory drive element and the rotatory drive element of the coupling unit is a first rotatory drive element,
that the translationally driven element of the sterile unit is a first translationally driven element and that the rotationally driven element is a first rotationally driven element,
that the coupling unit comprises a second translatory drive element for generating a translatory drive movement and a second rotatory drive element for generating a rotatory drive movement,
that the sterile unit has a second translationally driven element couplable to the second translatory drive element and a second rotationally driven element couplable to the second rotatory drive element,
that the sterile lock connected to the coupling unit shields the first and the second translatory drive elements and the first and second rotatory drive elements in a sterile manner before the sterile unit is connected to the sterile lock and after the sterile unit has been separated from the sterile lock.

7. The device according to claim 1, wherein the translationally driven element is movable into an initial position by means of the restoring force of an elastically deformable element, and that this restoring force moves the translationally driven element into its initial position after separating the sterile unit from the sterile lock.

8. The device according to claim 1, wherein the coupling unit has at least one position sensor for detecting at least one rotary angle position of the rotationally driven element.

9. The device according to claim 1, wherein the coupling unit has a separate drive unit for each drive element.

10. The device according to claim 1, wherein the driven elements of the sterile unit are arranged successively along the longitudinal axis of the surgical instrument,
wherein the driven elements are arranged, starting from the proximal end of the surgical instrument, in the order of, rotationally driven element, translationally driven element and thereafter optionally electrical contacts and/or an optical interface, wherein the coupling unit comprises, electrical contacts and/or an optical interface.

11. The device of claim 1, wherein the rotatory drive element is directly connected to the rotationally driven element, and the translatory drive element is directly connected to the translatory driven element.

12. An arrangement for robot-assisted surgery, in particular for a telerobot-assisted procedure within a sterile area, comprising
at least one device according to claim 1,
at least one display unit which outputs at least one image of an operating area in real time, at least one input device for the input of at least one input command, a control unit which positions the manipulator arm and the sterile unit connected via the sterile lock to the coupling unit of the manipulator arm dependent on the input command by means of at least one drive unit.

13. A device for robot-assisted surgery, comprising at least one non-sterile manipulator arm having a coupling unit with drive elements, a sterile instrument unit arranged in a sterile area and comprising a surgical instrument and a sterile unit for coupling the surgical instrument to the drive elements of the coupling unit, a sterile cover for shielding at least a part of the manipulator arm from the sterile area, wherein the coupling unit comprises a translatory drive element for generating a translatory drive movement and a rotatory drive element for generating a rotatory drive movement, that the sterile unit has a translationally driven element couplable to the translatory drive element and a rotationally driven element couplable to the rotatory drive element, that the sterile cover comprises a sterile lock which is connectable to the coupling unit and to the sterile unit, that the sterile lock connected to the coupling unit shields the translatory drive element and the rotatory drive element in a sterile manner before the sterile unit is connected to the sterile lock and after the sterile unit has been separated from the sterile lock;

wherein the coupling unit moves the translatory drive element into an initial position after the sterile unit has been separated from the sterile lock, wherein the translatory drive element arranged in its initial position is automatically brought into direct engagement with the translationally driven element arranged in an initial position when connecting the sterile unit to the sterile lock that is connected to the coupling unit.

14. A device for robot-assisted surgery, comprising at least one non-sterile manipulator arm having a coupling unit with drive elements, a sterile instrument unit arranged in a sterile area and comprising a surgical instrument and a sterile unit for coupling the surgical instrument to the drive elements of the coupling unit, a sterile cover for shielding at least a part of the manipulator arm from the sterile area, wherein the coupling unit comprises a translatory drive element for generating a translatory drive movement and a rotatory drive element for generating a rotatory drive movement, that the sterile unit has a translationally driven element couplable to the translatory drive element and a rotationally driven element couplable to the rotatory drive element, that the sterile cover comprises a sterile lock which is connectable to the coupling unit and to the sterile unit, that the sterile lock connected to the coupling unit shields the translatory drive element and the rotatory drive element in a sterile manner before the sterile unit is connected to the sterile lock and after the sterile unit has been separated from the sterile lock;

wherein the rotationally driven element includes a first rotationally driven element and a second rotationally driven element, wherein the translationally driven element includes a first translationally driven element and a second translationally driven element, wherein the second rotationally driven element is connected in a rotationally fixed manner to an outer instrument shaft for rotation thereof, that the second translationally driven element is connected to a first inner instrument shaft arranged so as to be movable lengthwise in the outer instrument shaft in the direction of the longitudinal axis of the outer instrument shaft, wherein, when the first inner instrument shaft is moved, an end effector of the surgical instrument is pivotable about a tilt axis, that the first rotationally driven element is connected in a rotationally fixed manner to a second inner instrument shaft arranged in the first inner instrument shaft, wherein, when the second inner instrument shaft is rotated, a rotation of the end effector is caused independent of the outer instrument shaft, that the first translationally driven element is connected to a third inner instrument shaft arranged so as to be movable lengthwise relative to the second inner instrument shaft in the second inner instrument shaft for actuating arms of the end effector which are movable relative to each other.

15. The device according to claim 14, wherein the arms of the end effector are cutting arms, gripping arms, and/or needle holder arms.

16. The device according to claim 14, wherein the arms of the end effector are arranged electrically insulated to each other, that the arms are each connected in an electrically conductive manner to one cable, which cables are passed through the third inner instrument shaft.

* * * * *